(12) United States Patent
Iwasawa et al.

(10) Patent No.: US 7,288,359 B2
(45) Date of Patent: *Oct. 30, 2007

(54) RADIATION-SENSITIVE RESIN COMPOSITION

(75) Inventors: Haruo Iwasawa, Mie (JP); Akihiro Hayashi, Mie (JP); Tsutomu Shimokawa, Mie (JP)

(73) Assignee: JSR Corporation, Tokyo (JP)

( * ) Notice: Subject to any disclaimer, the term of this patent is extended or adjusted under 35 U.S.C. 154(b) by 606 days.

This patent is subject to a terminal disclaimer.

(21) Appl. No.: 10/309,017

(22) Filed: Dec. 4, 2002

(65) Prior Publication Data

US 2003/0170561 A1    Sep. 11, 2003

(30) Foreign Application Priority Data

Dec. 5, 2001  (JP)  .............................. 2001-371311

(51) Int. Cl.
*G03C 1/73*    (2006.01)
*G03F 7/039*    (2006.01)

(52) U.S. Cl. .................. 430/270.1; 430/326; 430/905; 430/921; 430/925

(58) Field of Classification Search ............. 430/270.1, 430/905, 907, 914, 921, 923, 925, 325, 326
See application file for complete search history.

(56) References Cited

U.S. PATENT DOCUMENTS

| | | | |
|---|---|---|---|
| 6,387,590 B1 * | 5/2002 | Mizutani et al. | 430/270.1 |
| 6,531,260 B2 | 3/2003 | Iwasawa et al. | 430/270.1 |
| 7,108,955 B2 * | 9/2006 | Iwasawa et al. | 430/270.1 |
| 2003/0113658 A1 * | 6/2003 | Ebata et al. | 430/270.1 |

FOREIGN PATENT DOCUMENTS

| | | |
|---|---|---|
| EP | 1 142928 A1 * | 10/2001 |
| JP | 5323611 | 12/1993 |
| JP | 8160623 | 6/1996 |
| JP | 11060733 | 3/1999 |
| JP | 2001-215706 * | 8/2001 |
| WO | WO 02/090423 A1 * | 11/2002 |

OTHER PUBLICATIONS

English abstract for WO 02/090423—Chemical Abstract (access No. 137:370796).*
Machine-assisted English translation of JP 2001-215706, provided by JPO.*
Kunz et al., "Outlook for 157-nm Resist Design", J. Photopolym. Sci. Technol. 12, 4, 561-570 (1999).

* cited by examiner

*Primary Examiner*—Sin Lee
(74) *Attorney, Agent, or Firm*—Merchant & Gould, P.C.; Christopher W. Raimund

(57) ABSTRACT

A radiation-sensitive resin composition comprising (A) an acid-dissociable group-containing polysiloxane and (B) a photoacid generator containing trifluoromethane sulfonic acid or a compound which generates an acid of the following formula (I),

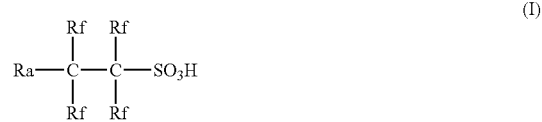

wherein Rf individually represents a fluorine atom or a trifluoromethyl group, and Ra represents a hydrogen atom, a fluorine atom, a linear or branched alkyl group having 1-20 carbon atoms, or a linear or branched fluoroalkyl group having 1-20 carbon atoms, a substituted or unsubstituted monovalent cyclic hydrocarbon group having 3-20 carbon atoms, or a substituted or unsubstituted monovalent cyclic fluoro-hydrocarbon group having 3-20 carbon atoms. The radiation-sensitive resin composition of the present invention exhibits superior resolution, while maintaining high transparency to radiations and high dry etching resistance. The resin composition thus can greatly contribute to the lithography process that will become more and more minute in the future.

13 Claims, No Drawings

RADIATION-SENSITIVE RESIN COMPOSITION

BACKGROUND OF THE INVENTION

1. Field of the Invention

The present invention relates to a radiation-sensitive resin composition suitable for microprocessing using various types of radiation such as deep ultraviolet radiation, electron beams, and X-rays.

2. Description of Background Art

A recent strong demand for high density and highly integrated LSIs (large-scale integrated circuits) radically accelerates miniaturization of wiring patterns.

Using short wave rays in a lithographic process is one method for miniaturizing wiring patterns. In recent years, deep ultraviolet rays typified by a KrF excimer laser (wavelength: 248 nm) or an ArF excimer laser (wavelength: 193 nm), electron beams, X rays, and the like are being used in place of ultraviolet rays such as g-line (wavelength: 436 nm) and i-line (wavelength: 365 nm).

Novolac resins, poly(vinylphenol), and the like have been used as resin components for conventional resist compositions. However, since these resins exhibit strong absorbance at a wavelength of 193 nm due to inclusion of aromatic rings in the structure, a lithographic process by an ArF excimer laser using these resins cannot provide high accuracy corresponding to high photosensitivity, high resolution, and a high aspect ratio.

Therefore, a resin for use in a resist, transparent to a wavelength of 193 nm or less and exhibiting dry etching resistance equivalent to or more excellent than aromatic rings, has been desired. A siloxane polymer is one such resin. R. R. Kunz et al. of the MIT have reported their research results showing excellent transparency of a polysiloxane wat a wavelength of 193 nm or less, particularly at 157 nm, commenting on superiority of this polymer as a resist material in a lithographic process using radiation at a wavelength of 193 nm or less (J. Photopolym. Sci. Technol., Vol. 12, No. 4, 1999). Moreover, polysiloxanes are known to exhibit excellent dry etching resistance. In particular, a resist containing polyorganosilsesquioxane having a ladder structure is known to possess high plasma resistance.

Several resist materials using a siloxane polymer have also been reported. For example, Japanese Patent Application Laid-open No. 323611/1993 discloses a radiation-sensitive resin composition comprising a polysiloxane having an acid-dissociable group such as a carboxylic acid ester group, phenol ether group, etc., on the side chain, bonded to a silicon atom via one or more carbon atoms. Japanese Patent Application Laid-open No. 160623/1996 discloses a positive tone resist using a polymer in which the carboxyl group of poly(2-carboxyethylsiloxane) is protected with an acid-dissociable group such as a t-butyl group. Japanese Patent Application Laid-open No. 60733/1999 discloses a resist resin composition in which a polyorganosilsesquioxane having an acid-decomposable ester group is used.

However, conventional resist materials using a siloxane polymer have not been satisfactory, particularly in the resolution performance.

An object of the present invention relates to a radiation-sensitive resin composition comprising an acid-dissociable group-containing polysiloxane as a resin component and suitable for use particularly as a chemically-amplified resist with excellent resolution.

SUMMARY OF THE INVENTION

The present invention provides a radiation-sensitive resin composition comprising (A) an acid-dissociable group-containing polysiloxane and (B) a photoacid generator containing, as an essential component, trifluoromethane sulfonic acid or a compound which generates an acid of the following formula (I),

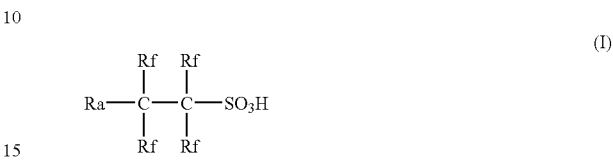

wherein Rf individually represents a fluorine atom or a trifluoromethyl group and Ra represents a hydrogen atom, a fluorine atom, a linear or branched alkyl group having 1-20 carbon atoms, or a linear or branched fluoroalkyl group having 1-20 carbon atoms, a monovalent cyclic hydrocarbon group having 3-20 carbon atoms, or a monovalent cyclic fluoro-hydrocarbon group having 3-20 carbon atoms, the monovalent cyclic hydrocarbon group and monovalent cyclic fluoro-hydrocarbon group being either substituted or unsubstituted.

Trifluoromethane sulfonic acid and the compound which generates the acid of the above formula (I) are hereinafter referred to as "acid generator (B1)." The acid of the above formula (I) is hereinafter referred to as "acid (I)."

In one embodiment of the present invention, the acid-dissociable group-containing polysiloxane (A) is a polymer containing at least one structural unit selected from the structural unit of the following formula (1) and the structural unit of the following formula (2),

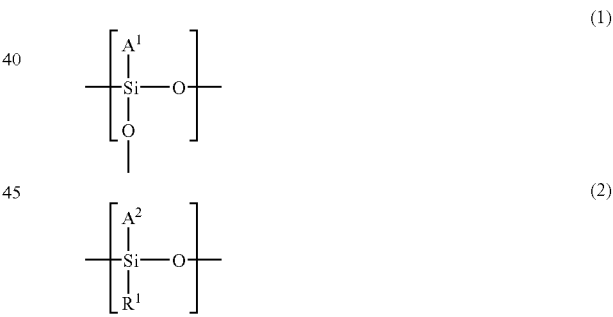

wherein $A^1$ and $A^2$ individually represent a monovalent organic group having an acid-dissociable group which dissociates by the action of an acid and $R^1$ represents a linear, branched, or cyclic alkyl group having 1-10 carbon atoms or a linear, branched, or cyclic haloalkyl group having 1-10 carbon atoms.

In another embodiment of the present invention, the essential component for the photoacid generator is the compound which generates the acid (I).

An onium salt is particularly preferable among the compounds generating the acid (I).

In the above formula (I), Ra is preferably a substituted or unsubstituted monovalent cyclic hydrocarbon group having 3-20 carbon atoms or a substituted or unsubstituted monovalent cyclic fluoro-hydrocarbon group having 3-20 carbon atoms.

In still another embodiment of the present invention, the composition further comprises, in addition to the acid generator (B1), at least one acid generator (B2) selected from the group consisting of the compounds which generate an acid of the following formula (II), (III), or (IV):

wherein, in the formula (II), Rf represents a fluorine atom or a trifluoromethyl group, Rf' represents a hydrogen atom, fluorine atom, methyl group, or trifluoromethyl group, and Rb represents a hydrogen atom, a linear or branched alkyl group having 1-20 carbon atoms, a substituted or unsubstituted monovalent cyclic hydrocarbon group having 3-20 carbon atoms, or a substituted or unsubstituted monovalent cyclic fluoro-hydrocarbon group having 3-20 carbon atoms; in the formula (III), Rs represents a linear or branched alkyl group having 1-20 carbon atoms or a substituted or unsubstituted monovalent cyclic hydrocarbon group having 3-20 carbon atoms; and in the formula (IV), Rc represents a linear or branched alkyl group having 1-20 carbon atoms, a linear or branched fluoroalkyl group having 1-20 carbon atoms, a substituted or unsubstituted monovalent cyclic hydrocarbon group having 3-20 carbon atoms, or a substituted or unsubstituted monovalent cyclic fluoro-hydrocarbon group having 3-20 carbon atoms.

DETAILED DESCRIPTION OF THE INVENTION AND PREFERRED EMBODIMENTS

The present invention will be described in detail below.

(A) Acid-dissociable Group-containing Polysiloxane

As an acid-dissociable group-containing polysiloxane of the present invention, an alkali insoluble or difficultly alkali soluble acid-dissociable group-containing polysiloxane can be given. A polymer having at least one structural unit selected from the structural unit of the above formula (1) (hereinafter referred to as "structural unit (1)") and the structural unit of the above formula (2) (hereinafter referred to as "structural unit (2)") is preferable. Such a polymer is hereinafter referred to as "polysiloxane ($\alpha$)."

As the monovalent organic group having an acid-dissociable group dissociable by the action of an acid represented by $A^1$ in the formula (1) or $A^2$ in the formula (2), the groups which are stable under the reaction conditions for preparing the polysiloxane ($\alpha$), such as a linear or branched $C_{1-20}$ hydrocarbon group having one or more acid-dissociable groups dissociate in the presence of an acid to produce preferably a carboxyl group, phenolic hydroxyl group, or alcoholic hydroxyl group, or a monovalent cyclic $C_{4-30}$ hydrocarbon group having the one or more acid-dissociable groups, can be given.

The groups of the following formula (3) are preferable as the acid-dissociable groups.

$$-P-Q-R^2 \quad (3)$$

wherein P indicates a single bond, methylene group, difluoromethylene group, substituted or unsubstituted, linear or branched alkylene group having 2-20 carbon atoms, substituted or unsubstituted, divalent aromatic group having 6-20 carbon atoms, or substituted or unsubstituted, divalent alicyclic group having 3-20 carbon atoms, Q represents a group —COO— or —O—, and $R^2$ represents a monovalent organic group dissociable by the action of an acid to produce hydrogen atoms.

As examples of the linear or branched alkylene groups having 2-20 carbon atoms represented by P in the formula (3), ethylene group, propylene group, trimethylene group, tetramethylene group, and the like can be given; as divalent aromatic groups having 6-20 carbon atoms, phenylene group, naphthylene group, and the like can be given; and as divalent alicyclic groups having 3-20 carbon atoms, cycloalkylene groups such as cyclopropylene group, cyclobutylene group, cyclohexylene group, and divalent hydrocarbon groups having a bridged alicyclic skeleton such as a norbornane skeleton, tricyclodecane skeleton, tetracyclodecane skeleton, and adamantane skeleton can be given.

As substituents on these alkylene groups, divalent aromatic groups, or divalent alicyclic groups, a fluorine atom and a linear or branched fluoroalkyl group having 1-10 carbon atoms are preferable.

These divalent aromatic groups and divalent alicyclic groups may also contain a methylene group, difluoromethylene group, linear or branched alkylene group having 1-10 carbon atoms, or linear or branched fluoroalkylene group having 1-10 carbon atoms.

As the group P in the formula (3), a single bond, methylene group, difluoromethylene group, divalent hydrocarbon group having a tricyclodecane skeleton and a fluoride derivative thereof, divalent hydrocarbon group having an adamantane skeleton and a fluoride derivative thereof, divalent hydrocarbon group having a norbornane skeleton and a fluoride derivative thereof, and the like can be given. Of these, the divalent hydrocarbon group having a norbornane skeleton and a fluoride derivative thereof are preferable.

The following groups can be given as examples of the monovalent organic group dissociable by the action of an acid to produce hydrogen atoms represented by $R^2$: linear, branched, or cyclic alkyl groups such as a methyl group, ethyl group, n-propyl group, i-propyl group, n-butyl group, i-butyl group, sec-butyl group, t-butyl group, cyclopentyl group, 1-methylcyclopentyl group, 1-ethylcyclopentyl group, cyclohexyl group, 1-methylcyclohexyl group, 1-ethylcyclohexyl group, 4-t-butylcyclohexyl group, cycloheptyl group, and cyclooctyl group; alkyl substituted adamantyl groups such as a 1-methyladamantyl group and 1-ethyladamantyl group; aralkyl groups such as a benzyl group, 4-t-butylbenzyl group, phenethyl group, and 4-t-butylphenethyl group; organocarbonyl groups such as a t-butoxycarbonyl group, methoxycarbonyl group, ethoxycarbonyl group, i-propoxycarbonyl group, 2-(trimethylsilyl)ethylcarbonyl group, i-butylcarbonyl group, vinylcarbonyl group, allylcarbonyl group, benzylcarbonyl group, and 4-ethoxy-1-naphthylcarbonyl group; organic groups combining with the oxygen atom in the formula (3) to form an acetal structure such as a methoxymethyl group, methylthiomethyl group, ethoxymethyl group, t-butoxymethyl group, (phenyldimethylsilyl)methoxymethyl group, benzyloxymethyl group, t-butoxymethyl group, siloxymethyl group, 2-methoxyethoxymethyl group, 2,2,2-trichloroethoxymethyl group, bis(2-chloroethoxy)methyl group, 1-methoxycyclohexyl group, tetrahydropyranyl group, 4-methoxytetrahydropyranyl group, tetrahydrofuranyl group, 1-methoxyethyl group, 1-ethoxyethyl group, 1-(2-chloroethoxy)ethyl group, 1-methyl-1-methoxyethyl group, 1-methyl-1-benzyloxyethyl group, 1-(2-chloroethoxy)ethyl group, and 1-methyl-1-benzyloxy-2-fluoroethyl group; and silyl groups such as a trimethylsilyl group, triethylsilyl group, dimethylethylsilyl group, t-butyldimethylsilyl group, t-butyldiphenylsilyl group, triphenylsilyl group, diphenylmethylsilyl group, and t-butylmethoxyphenylsilyl group.

Of these monovalent organic groups dissociating by the action of an acid to produce hydrogen atoms, the t-butyl group, tetrahydropyranyl group, tetrahydrofuranyl group, methoxymethyl group, ethoxymethyl group, 1-methoxyethyl group, 1-ethoxyethyl group, t-butyldimethylsilyl group, and the like are preferable.

As examples of the linear, branched, or cyclic alkyl group having 1-10 carbon atoms represented by $R^1$ in the formula (2), a methyl group, ethyl group, n-propyl group, i-propyl group, cyclopentyl group, and cyclohexyl group can be given. As examples of the linear, branched, or cyclic haloalkyl group having 1-10 carbon atoms, trifluoromethyl group, pentafluoroethyl group, heptafluoro-n-propyl group, heptafluoro-i-propyl group, and perfluorocyclohexyl group can be given.

As $R^1$ in the formula (2), a methyl group, ethyl group, trifluoromethyl group, pentafluoroethyl group, and the like are preferable.

The polysiloxane (α) may also contain one or more other structural units having no acid-dissociable groups.

As such other structural units, the structural unit of the following formula (4) (hereinafter referred to as "structural unit (4)"), the structural unit of the following formula (5) (hereinafter referred to as "structural unit (5)"), and the like can be given:

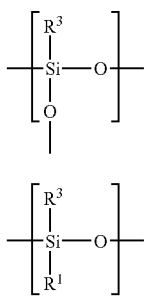

wherein $R^3$ individually represents a monovalent group of the formula —P—H, —P—F, or —P-Q-H (wherein P individually represents the same group defined in the formula (3) and Q is the same as defined in the formula (3)) and $R^1$ is the same as defined in the formula (2).

As preferable specific examples of the group represented by $R^3$ in the formulas (4) and (5), the groups of the following formulas (6) to (11), a methyl group, ethyl group, norbornyl group, tetracyclodecanyl group, and the like can be given:

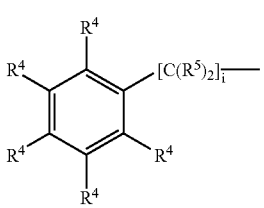

wherein $R^4$ individually represents a fluorine atom, fluoroalkyl group having 1-10 carbon atoms, hydrogen atom, halogen atom other than fluorine atom, alkyl group having 1-10 carbon atoms, or monovalent organic group having an acid-dissociable group dissociable by the action of an acid, $R^5$ individually represents a fluorine atom, fluoroalkyl group having 1-10 carbon atoms, hydrogen atom, halogen atom other than fluorine atom, or alkyl group having 1-10 carbon atoms, provided that at least one of five $R^4$ groups and 2i $R^5$ groups represents a fluorine atom or fluoroalkyl group having 1-10 carbon atoms, and i is an integer of 0 to 10,

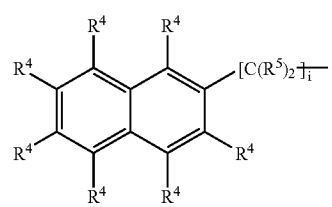

wherein $R^4$ individually represents a fluorine atom, fluoroalkyl group having 1-10 carbon atoms, hydrogen atom, halogen atom other than fluorine atom, alkyl group having 1-10 carbon atoms, or monovalent organic group having an acid-dissociable group dissociable by the action of an acid, $R^5$ individually represents a fluorine atom, fluoroalkyl group having 1-10 carbon atoms, hydrogen atom, halogen atom other than fluorine atom, or alkyl group having 1-10 carbon atoms, provided that at least one of seven $R^4$ groups and 2i $R^5$ groups represents a fluorine atom or fluoroalkyl group having 1-10 carbon atoms, and i is an integer of 0 to 10,

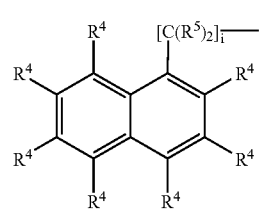

wherein $R^4$ individually represents a fluorine atom, fluoroalkyl group having 1-10 carbon atoms, hydrogen atom, halogen atom other than fluorine atom, alkyl group having 1-10 carbon atoms, or monovalent organic group having an acid-dissociable group dissociable by the action of an acid, $R^5$ individually represents a fluorine atom, fluoroalkyl group having 1-10 carbon atoms, hydrogen atom, halogen atom other than fluorine atom, or alkyl group having 1-10 carbon atoms, provided that at least one of seven $R^4$ groups and 2i $R^5$ groups represents a fluorine atom or fluoroalkyl group having 1-10 carbon atoms, and i is an integer of 0 to 10,

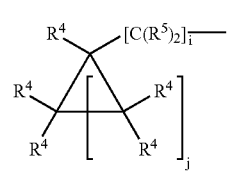

wherein $R^4$ individually represents a fluorine atom, fluoroalkyl group having 1-10 carbon atoms, hydrogen atom, halogen atom other than fluorine atom, alkyl group having 1-10 carbon atoms, or monovalent organic group having an acid-dissociable group dissociable by the action of an acid, $R^5$ individually represents a fluorine atom, fluoroalkyl group having 1-10 carbon atoms, hydrogen atom, halogen atom other than fluorine atom, or alkyl group having 1-10 carbon atoms, provided that at least one of (3+2j) $R^4$ groups and 2i $R^5$ groups represents a fluorine atom or fluoroalkyl group having 1-10 carbon atoms, i is an integer of 0 to 10, and j is an integer of 1 to 18,

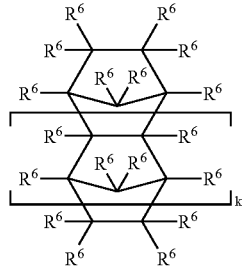

(10)

wherein one of (12+6 k) $R^6$ groups represents a group —[C($R^5$)$_2$]$_i$— and the remaining $R^6$ groups individually represent a fluorine atom, fluoroalkyl group having 1-10 carbon atoms, hydrogen atom, halogen atom other than fluorine atom, alkyl group having 1-10 carbon atoms, or monovalent organic group having an acid-dissociable group dissociable by the action of an acid, $R^5$ individually represents a fluorine atom, fluoroalkyl group having 1-10 carbon atoms, hydrogen atom, halogen atom other than fluorine atom, or alkyl group having 1-10 carbon atoms, provided that at least one of the remaining (11+6 k) $R^6$ groups and 2i $R^5$ groups represents a fluorine atom or fluoroalkyl group having 1-10 carbon atoms, i is an integer of 0 to 10, and k is an integer of 0 to 3, and

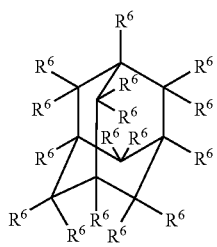

(11)

wherein one of 16 $R^6$ groups represents a group —[C($R^5$)$_2$]$_i$— and the remaining $R^6$ groups individually represent a fluorine atom, fluoroalkyl group having 1-10 carbon atoms, hydrogen atom, halogen atom other than fluorine atom, alkyl group having 1-10 carbon atoms, or monovalent organic group having an acid-dissociable group dissociable by the action of an acid and $R^5$ individually represents a fluorine atom, fluoroalkyl group having 1-10 carbon atoms, hydrogen atom, halogen atom other than fluorine atom, or alkyl group having 1-10 carbon atoms, provided that at least one of the remaining 15 $R^6$ groups and 2i $R^5$ groups represents a fluorine atom or fluoroalkyl group having 1-10 carbon atoms.

The polysiloxane (α) can be prepared by a process comprising a polycondensation step of at least one silane compound selected from the compounds of the following formula (12) (hereinafter referred to as "silane compound (12)"), a linear or cyclic oligomer produced by partial condensation of the silane compound (12), the compounds of the following formula (13) (hereinafter referred to as "silane compound (13)"), and a linear or cyclic oligomer produced by partial condensation of the silane compound (13), in the presence of an acid catalyst or a base catalyst, preferably in the presence of an acid catalyst,

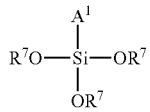

(12)

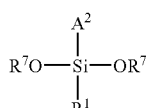

(13)

wherein $A^1$ is the same as defined in the above formula (1), and $A^2$ and $R^1$ are the same as defined in the above formula (2), and $R^7$ groups individually represent a monovalent saturated hydrocarbon group having 1-10 carbon atoms.

As $R^7$ in the formulas (12) and (13), an alkyl group having 1-10 carbon atoms is preferable, with a methyl group and ethyl group being particularly preferable.

Here, the "linear or cyclic oligomer prepared by partial condensation of the silane compound (12)" indicates a linear oligomer of usually 2-10 molecules, preferably 2-5 molecules, or a cyclic oligomer of usually 3-10 molecules, preferably 3-5 molecules, each oligomer being formed by condensing two $R^7$O—Si groups in the silane compound (12). The "linear or cyclic oligomer prepared by partial condensation of the silane compound (13)" indicates a linear oligomer of usually 2-10 molecules, preferably 2-5 molecules, or a cyclic oligomer of usually 3-10 molecules, preferably 3-5 molecules, each oligomer being formed by condensing two $R^7$O—Si groups in the silane compound (13).

The silane compounds (12) and (13) may be used either individually or in combination of two or more.

In the present invention, one or more other silane compounds may be used together with the silane compounds (12) and/or (13) or partial condensates of these silane compounds.

As examples of other silane compounds, a silane compound of the following formula (14) (hereinafter referred to as "silane compound (14)"), a silane compound of the following formula (15) (hereinafter referred to as "silane compound (15)"), and partial condensates of these silane compounds can be given.

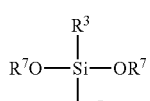

(14)

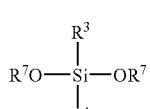

(15)

wherein $R^1$ is the same as defined in the above formula (2), $R^3$ is the same as defined in the above formulas (4) and (5), and $R^7$ is the same as defined in the above formulas (12) and (13).

As $R^7$ in the formulas (14) and (15), an alkyl group having 1-10 carbon atoms is preferable, with a methyl group and ethyl group being particularly preferable.

"Partial condensate" herein indicates a linear oligomer formed from 2-10, preferably 2-5, silane molecules, or a cyclic oligomer formed from 3-10, preferably 3-5, silane molecules.

In the present invention, if at least one compound selected from the group consisting of the silane compound (14), silane compound (15), and their partial condensates, preferably the silane compound (14) or its partial condensate, is condensed together with the silane compound (12) and/or silane compound (13), or their partial condensates, the molecular weight and glass transition temperature (Tg) of the resulting polysiloxane (α) can be adequately controlled so that transparency at the wavelength of 193 nm or less, particularly at the wavelength of 193 nm or 157 nm, can be further improved.

The total amount of the silane compound (14), silane compound (15), and their partial condensates is usually 1 mol % or more, preferably 5-95 mol %, and particularly preferably 10-90 mol %, for 100 wt % of all silane compounds. If this total amount is less than 1 mol %, transparency to light, particularly to light at a wavelength of 193 nm or 157 nm, tends to be impaired.

As examples of the inorganic acids among the acidic catalysts used for preparing polysiloxane (α), hydrochloric acid, sulfuric acid, nitric acid, boric acid, phosphoric acid, titanium tetrachloride, zinc chloride, and aluminum chloride can be given. As examples of organic acids, formic acid, acetic acid, n-propionic acid, butyric acid, valeric acid, oxalic acid, malonic acid, succinic acid, maleic acid, fumaric acid, adipic acid, phthalic acid, terephthalic acid, acetic anhydride, maleic anhydride, citric acid, benzenesulfonic acid, p-toluenesulfonic acid, and methanesulfonic acid can be given.

Of these acidic catalysts, hydrochloric acid, sulfuric acid, acetic acid, oxalic acid, malonic acid, maleic acid, fumaric acid, acetic anhydride, maleic anhydride, and the like are preferable.

These acidic catalysts may be used either individually or in combination of two or more.

The acidic catalysts are usually used in the amount of 0.01-10,000 parts by weight, preferably 0.1-100 parts by weight, for 100 parts by weight of the silane compound.

As examples of inorganic bases among the basic catalysts used for preparing the polysiloxane (α), lithium hydroxide, sodium hydroxide, potassium hydroxide, calcium hydroxide, barium hydroxide, sodium hydrogencarbonate, potassium hydrogencarbonate, sodium carbonate, and potassium carbonate can be given.

The following compounds can be given as examples of organic bases: linear, branched, or cyclic monoalkylamines such as n-hexylamine, n-heptylamine, n-octylamine, n-nonylamine, n-decylamine, and cyclohexylamine; linear, branched, or cyclic dialkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; linear, branched, or cyclic trialkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, dicyclohexylmethylamine, and tricyclohexylamine; aromatic amines such as aniline, N-methylaniline, N,N-dimethylaniline, 2-methylaniline, 3-methylaniline, 4-methylaniline, 4-nitroaniline, diphenylamine, triphenylamine, and naphthylamine; aromatic diamines such as ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene; imidazoles such as imidazole, benzimidazole, 4-methylimidazole, and 4-methyl-2-phenylimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinamide, quinoline, 4-hydroxyquinoline, 8-oxyquinoline, and acridine; piperazines such as piperazine and 1-(2-hydroxyethyl)piperazine; and other nitrogen-containing heterocyclic compounds such as pyrazine, pyrazole, pyridazine, quinoxaline, purine, pyrrolidine, piperidine, morpholine, 4-methylmorpholine, 1,4-dimethylpiperazine, and 1,4-diazabicyclo[2.2.2]octane.

Of these basic catalysts, triethylamine, tri-n-propylamine, tri-n-butylamine, pyridine, and the like are preferable.

These basic catalysts may be used either individually or in combination of two or more. The basic catalysts are usually used in the amount of 0.01-10,000 parts by weight, preferably 0.1-1,000 parts by weight, for 100 parts by weight of the silane compound.

In the polycondensation reaction for preparing the polysiloxane (α), it is preferable that the silane compounds be first polycondensed in the presence of an acidic catalyst, and then a basic catalyst be added to promote the reaction. This mode of reaction ensures occurrence of a crosslinking reaction even if a silane compound possessing an acid-dissociable group that is unstable under the acidic conditions is used, whereby polysiloxane (α) having excellent properties such as a high molecular weight and a high glass transition temperature (Tg) can be obtained. In addition, it is possible to control the degree of crosslinking by adjusting the reaction conditions under basic conditions, whereby solubility of the resulting polysiloxane (α) in a developing solution can be controlled.

The polycondensation reaction under acidic conditions or basic conditions is preferably carried out in an inert gas atmosphere such as nitrogen or argon to obtain a pattern-forming layer less susceptible to a negative-tone reaction when forming a resist pattern.

The polycondensation reaction can be carried out either in the presence or in the absence of a solvent.

Given as examples of the solvents are: linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, and 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-secbutyl ether acetate, and propylene glycol mono-t-butyl ether acetate; alkyl 2-hydroxypropionates such as methyl 2-hydroxypropionate, ethyl 2-hydroxypropionate, n-propyl 2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; alkyl 3-alkoxypropionates such as methyl 3-methoxypropionate, ethyl 3-methoxypropionate, methyl 3-ethoxypropionate, and ethyl 3-ethoxypropionate; alcohols such as n-propyl alcohol, i-propyl alcohol, n-butyl alcohol, t-butyl alcohol, cyclohexanol, ethylene glycol monomethyl ether, ethylene glycol monoethyl ether, ethylene glycol mono-n-propyl ether, ethylene glycol mono-n-butyl ether, propylene glycol monomethyl ether, propylene glycol monoethyl ether, and propylene glycol mono-n-propyl ether; dialkylene glycol dialkyl ethers such as diethylene glycol dimethyl ether, diethylene glycol diethyl ether, diethylene glycol di-n-propyl ether, diethylene glycol di-n-butyl ether; ethylene glycol monoalkyl ether acetates such as ethylene glycol monomethyl ether acetate, ethylene glycol monoethyl ether acetate, and ethylene glycol mono-n-propyl ether acetate; aromatic hydrocarbons such as toluene and xylene; other esters such as ethyl 2-hydroxy-2-methylpropionate, ethyl ethoxyacetate, ethyl hydroxyacetate, methyl 2-hydroxy-3-methylbutyrate, butyl 3-methoxyacetate, butyl 3-methyl-3-methoxyacetate, butyl 3-methyl-3-methoxypropionate, butyl 3-methyl-3-methoxybutyrate, ethyl acetate, n-propyl acetate, n-butyl acetate, methyl acetoacetate, ethyl acetoacetate, methylpyruvate, and ethyl pyruvate; N-methylpyrrolidone, N,N-dimethylformamide, N,N-dimethylacetamide, benzyl ethyl ether, di-n-hexyl ether, diethylene glycol monomethyl ether, diethylene glycolmonoethyl ether, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate; and the like.

These solvents may be used either individually or in combinations of two or more.

These solvents are usually used in the amount of 2,000 parts by weight or less for 100 parts by weight of all of the silane compounds.

The polycondensation reaction can be preferably carried out either in the presence or absence of a solvent, such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, 2-octanone, cyclopentanone, 3-methylcyclopentanone, cyclohexanone, 2-methylcyclohexanone, 2,6-dimethylcyclohexanone, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, and ethylene glycol mono-n-propyl ether acetate.

In addition, water may be added to the reaction mixture of the polycondensation reaction. The amount of water to be added is usually 10,000 parts by weight or less for 100 parts by weight of all of the silane compounds.

Furthermore, hexamethyldisiloxane may be added to the reaction mixture of the polycondensation reaction to control the molecular weight of the resulting polysiloxane (α) and to increase stability.

The amount of hexamethyldisiloxane to be added is usually 500 parts by weight or less, and preferably 50 parts by weight or less, for 100 parts by weight of all of the silane compounds. If the amount of hexamethyldisiloxane exceeds 500 parts by weight, the resulting polymer tends to have a smaller molecular weight and a lower glass transition temperature (Tg).

The polycondensation reaction is carried out at a temperature of usually −50 to 300° C., and preferably 20 to 100° C., usually for a period of one minute to 100 hours.

In the polysiloxane (α), the total amount of the structural units (1) and (2) is usually 1-99 mol %, preferably 1-95 mol %, more preferably 5-80 mol %, and particularly preferably 10-60 mol % of the total amount of structural units. If the amount of the above structural units is less than 1 mol %, resolution during pattern formation tends to decrease. If the amount exceeds 99 mol %, adhesiveness with the under layer film tends to decrease.

The amount of the structural unit (1) is preferably 1-95 mol %, more preferably 5-80 mol %, and particularly preferably 10-60 mol % of the total amount of the structural units. If the amount of the structural unit (1) is less than 1 mol %, resolution during pattern formation may decrease. If the amount exceeds 95 mol %, transparency of the resulting polymer to radiation tends to decrease.

The amount of the structural unit (2) is preferably 95 mol % or less, more preferably 80 mol % or less, and particularly preferably 30 mol % or less of the total amount of the structural units. If the amount of the structural unit (2) is more than 95 mol %, the glass transition temperature (Tg) and transparency to radiation of the resulting polymer tend to decrease.

The total amount of the structural units (4) and (5) that are optionally incorporated in the polysiloxane (α) is preferably 5-95 mol %, more preferably 20-95 mol %, and particularly preferably 40-90 mol % of the total amount of the structural units. If the total amount is less than 5 mol %, transparency to radiation of the resulting polymer may decrease. If the amount exceeds 95 mol %, resolution during pattern formation may be impaired.

The polysiloxane (α) preferably has a ladder structure as part of the molecular structure. The ladder structure is principally introduced by the structural unit (1) or the structural unit (4).

The polystyrene-reduced weight average molecular weight (hereinafter called "Mw") of the acid-dissociable group-containing polysiloxane determined by gel permeation chromatography (GPC) is usually 500-100,000, preferably 500-50,000, and still more preferably 1,000-10,000. If the Mw of the acid-dissociable group-containing polysiloxane is less than 500, the glass transition temperature (Tg) of the resulting polymer tends to decrease. If the Mw exceeds 100,000, solubility of the resulting polymer in solvents tends to decrease.

The ratio of Mw to the polystyrene-reduced number average molecular weight (hereinafter referred to as "Mn") determined by gel permeation chromatography (GPC) (Mw/Mn) of the acid-dissociable group-containing polysiloxane is usually 2.5 or less, preferably 2 or less, and still more preferably 1.8 or less.

The glass transition temperature (Tg) of the acid-dissociable group-containing polysiloxane is usually 0-500° C., and preferably 50-250° C. If the glass transition temperature (Tg) of the acid-dissociable group-containing polysiloxane is less than 0° C., pattern formation may be difficult. If more than 500° C., solubility of the polymer in solvents tends to decrease.

In the present invention, the acid-dissociable group-containing polysiloxanes can be used either individually or in combination of two or more.

(B) Photoacid Generator

The photoacid generator of the present invention comprises, as an essential component, an acid generator (B1), a compound which generates trifluoromethane sulfonic acid or the acid of the above formula (I) (hereinafter referred to as "acid (I)") upon exposure to radiation such as deep ultraviolet rays, electron beams, and X-rays.

As examples of the photoacid generator (B1), onium salt compounds, sulfone compounds, sulfonic acid compounds, carboxylic acid compounds, diazoketone compounds, and halogen-containing compounds can be given. A combination of at least one photoacid generator (B1) and at least one compound selected from the following compounds (B2) is preferably used.

(B2) Compounds generating an acid of the following formula (II) ("acid (II)"), an acid of the following formula (III) ("acid (III)"), or an acid of the following formula (IV) ("acid (IV)") (hereinafter referred to as "photoacid generator (B2)"):

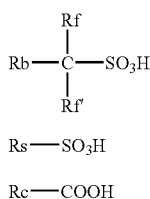

wherein, in the formula (II), Rf represents a fluorine atom or a trifluoromethyl group, Rf' represents a hydrogen atom, fluorine atom, methyl group, or trifluoromethyl group, and Rb represents a hydrogen atom, a linear or branched alkyl group having 1-20 carbon atoms, a substituted or unsubstituted monovalent cyclic hydrocarbon group having 3-20 carbon atoms, or a substituted or unsubstituted monovalent cyclic fluoro-hydrocarbon group having 3-20 carbon atoms; in the formula (III), Rs represents a linear or branched alkyl group having 1-20 carbon atoms or a substituted or unsubstituted monovalent cyclic hydrocarbon group having 3-20 carbon atoms; and in the formula (IV), Rc represents a linear or branched alkyl group having 1-20 carbon atoms, a linear or branched fluoroalkyl group having 1-20 carbon atoms, a substituted or unsubstituted monovalent cyclic hydrocarbon group having 3-20 carbon atoms, or a substituted or unsubstituted monovalent cyclic fluoro-hydrocarbon group having 3-20 carbon atoms.

As specific examples of the linear or branched alkyl group having 1-20 carbon atoms represented by Ra, Rb, Rs, or Rc in the formulas (I), (II), (III), and (IV), a methyl group, ethyl group, n-propyl group, i-propyl group, n-butyl group, i-butyl group, sec-butyl group, t-butyl group, n-pentyl group, n-hexyl group, n-heptyl group, and n-octyl group can be given.

As specific examples of the linear or branched fluoroalkyl group having 1-20 carbon atoms represented by Ra or Rc, a trifluoromethyl group, pentafluoroethyl group, heptafluoro-n-propyl group, heptafluoro-i-propyl group, nonafluoro-n-butyl group, nonafluoro-i-butyl group, nonafluoro-sec-butyl group, nonafluoro-t-butyl group, perfluoro-n-pentyl group, perfluoro-n-hexyl group, perfluoro-n-heptyl group, and perfluoro-n-octyl group can be given.

As examples of the monovalent cyclic hydrocarbon group having 3-20 carbon atoms, the monovalent cyclic fluoro-hydrocarbon group having 3-20 carbon atoms, or their substituted derivatives represented by Ra, Rb, Rs, or Rc groups of the following formulas (16)-(22) can be given:

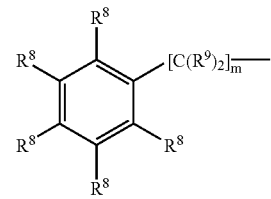

wherein $R^8$ individually represents a hydrogen atom, halogen atom, hydroxyl group, acetyl group, carboxyl group, nitro group, cyano group, primary amino group, secondary amino group, linear or branched alkoxyl group having 1-10 carbon atoms, linear or branched alkyl group having 1-10 carbon atoms, or linear or branched fluoroalkyl group having 1-10 carbon atoms, $R^9$ individually represents a hydrogen atom, halogen atom, linear or branched alkyl group having 1-10 carbon atoms, or a linear or branched fluoroalkyl group having 1-10 carbon atoms, and m is an integer of 0-10,

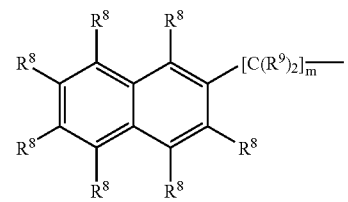

wherein $R^8$, $R^9$, and m are the same as defined in the formula (16),

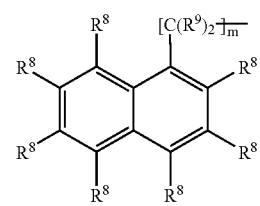

wherein $R^8$, $R^9$, and m are the same as defined in the formula (16),

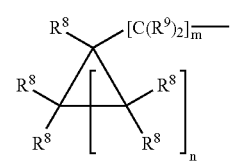

wherein $R^8$, $R^9$, and m are the same as defined in the formula (16), and n is an integer of 1-18,

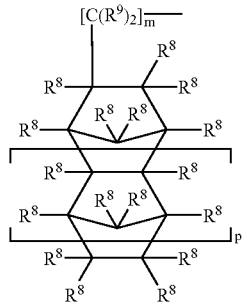

(20)

wherein $R^8$, $R^9$, and m are the same as defined in the formula (16), and p is an integer of 0-3,

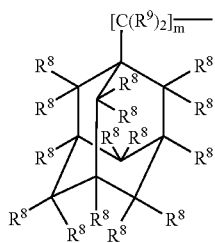

(21)

wherein $R^8$, $R^9$, and m are the same as defined in the formula (16), and

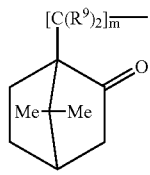

(22)

wherein $R^9$ and m are the same as defined in the formula (16), and Me is a methyl group.

Preferable examples of the acid (I) include trifluoromethanesulfonic acid, pentafluoroethanesulfonic acid, heptafluoro-n-propanesulfonic acid, nonafluoro-n-butanesulfonic acid, perfluoro-n-octanesulfonic acid, 1,1,2,2,-tetrafluoro-n-propanesulfonic acid, 1,1,2,2,-tetrafluoro-n-butanesulfonic acid, and 1,1,2,2-tetrafluoro-n-octanesulfonic acid, as well as acids produced by bonding a group —$CF_2CF_2SO_3H$, —$CF_2CF(CF_3)SO_3H$, —$CF(CF_3)CF_2SO_3H$, —$CF(CF_3)CF(CF_3)SO_3H$, —$C(CF_3)_3CF_2SO_3H$, or —$CF_2C(CF_3)_3SO_3H$ to the bonding site of the group of any of the formulas (16)-(22), for example, the acids of the following formula (I-1) to (I-10):

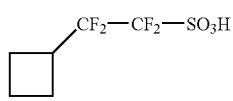

(I-1)

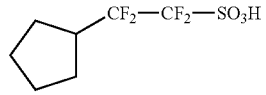

(I-2)

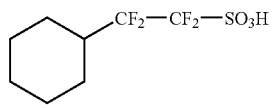

(I-3)

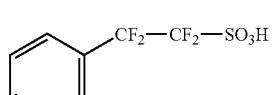

(I-4)

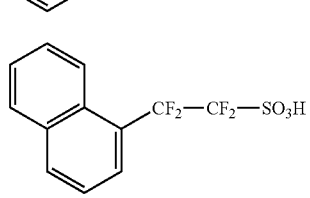

(I-5)

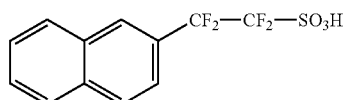

(I-6)

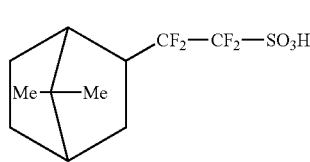

(I-7)

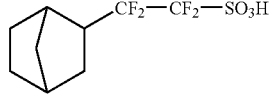

(I-8)

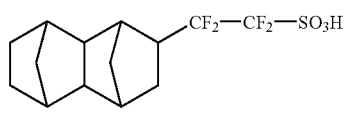

(I-9)

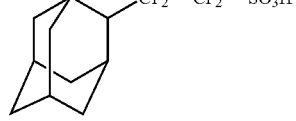

(I-10)

The following acids can be given as preferable examples of the acids (II) in the present invention:

1-fluoroethanesulfonic acid, 1-fluoro-n-propanesulfonic acid, 1-fluoro-n-butanesulfonic acid, 1-fluoro-n-octanesulfonic acid, 1,1-difluoroethanesulfonic acid, 1,1-difluoro-n-propanesulfonic acid, 1,1-difluoro-n-butanesulfonic acid, 1,1-difluoro-n-octanesulfonic acid, 1-trifluoromethyl-n-propanesulfonic acid, 1-trifluoromethyl-n-butanesulfonic acid, 1-trifluoromethyl-n-octanesulfonic acid, 1,1-bis(trifluoromethyl)ethanesulfonic acid, 1,1-bis(trifluoromethyl)-n-propanesulfonic acid, 1,1-bis(trifluoromethyl)-n-butanesulfonic acid, and 1,1-bis(trifluoromethyl)-n-octanesulfonic acid, as well as acids produced by bonding a group —$CF_2SO_3H$, —$CHFSO_3H$, —$CH(CF_3)SO_3H$, or —$C(CF_3)_2SO_3H$ to the bonding site of the group of any of the formulas (16)-(22), for example, the acids of the following formulas (II-1) to (II-40):

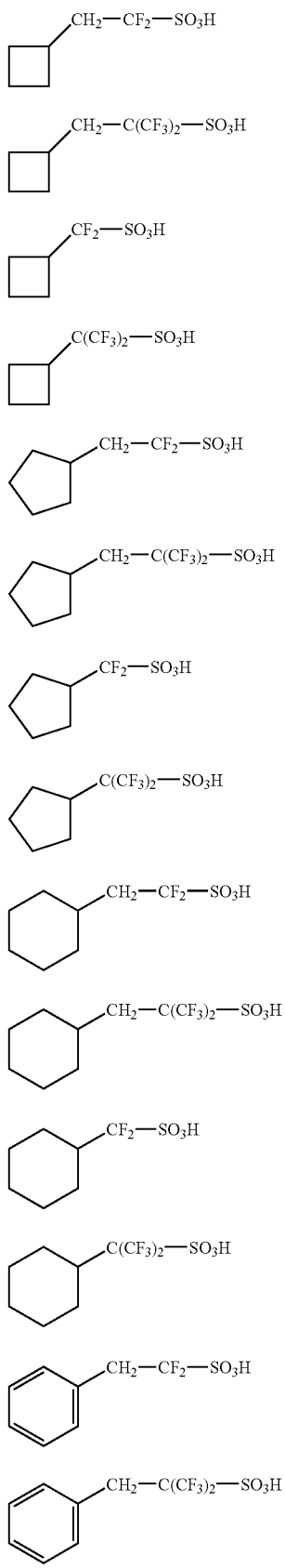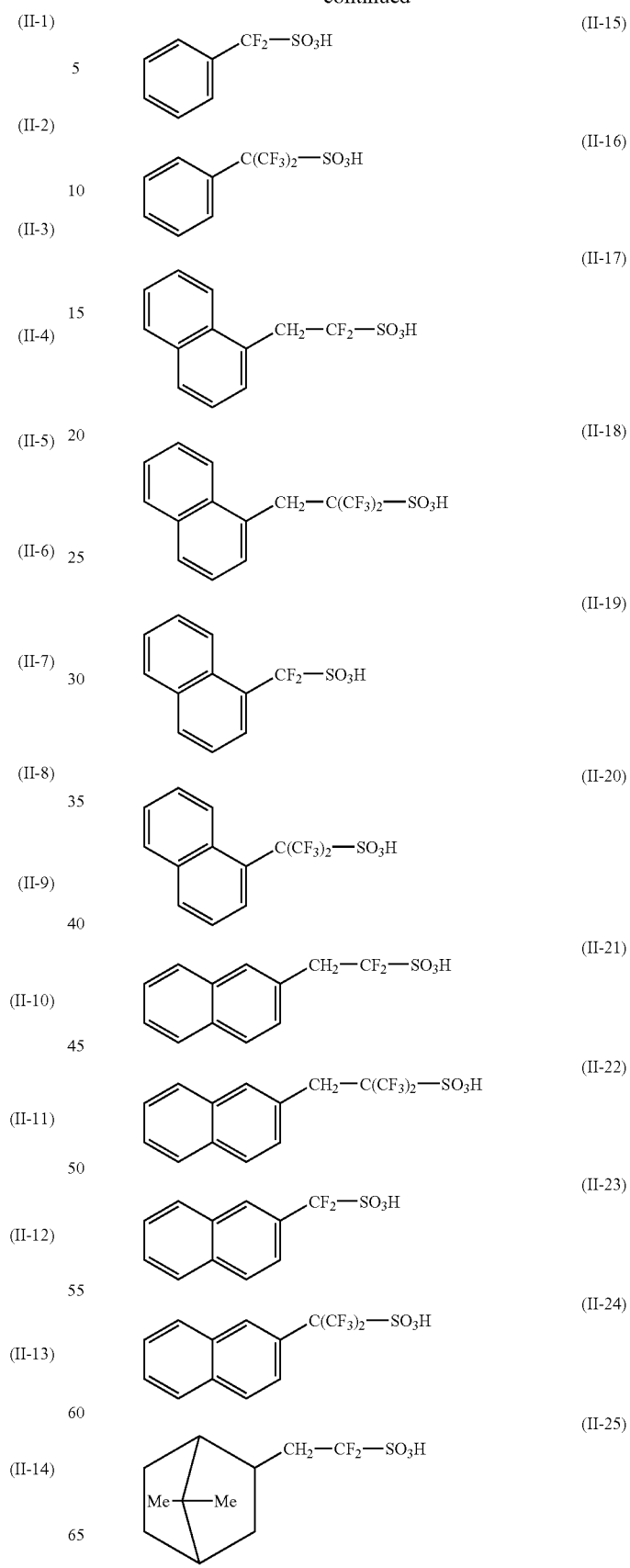

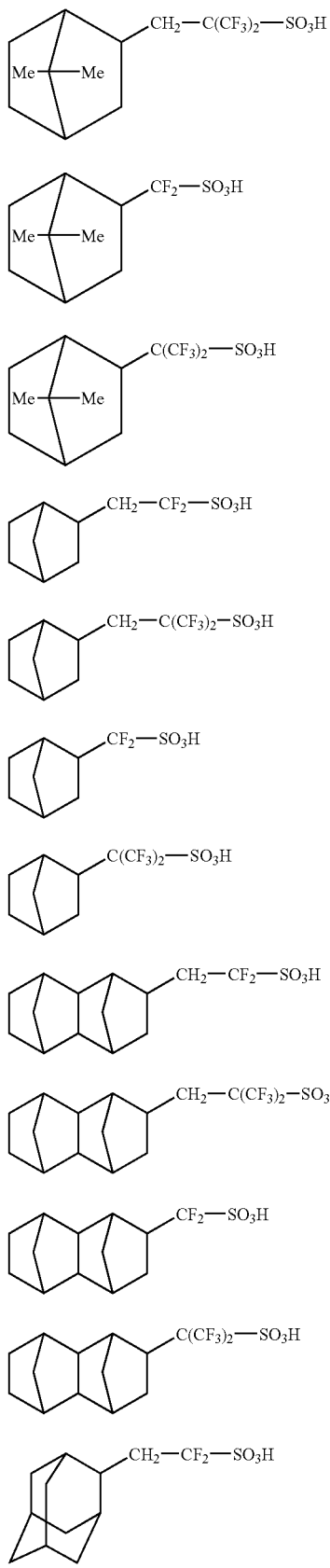

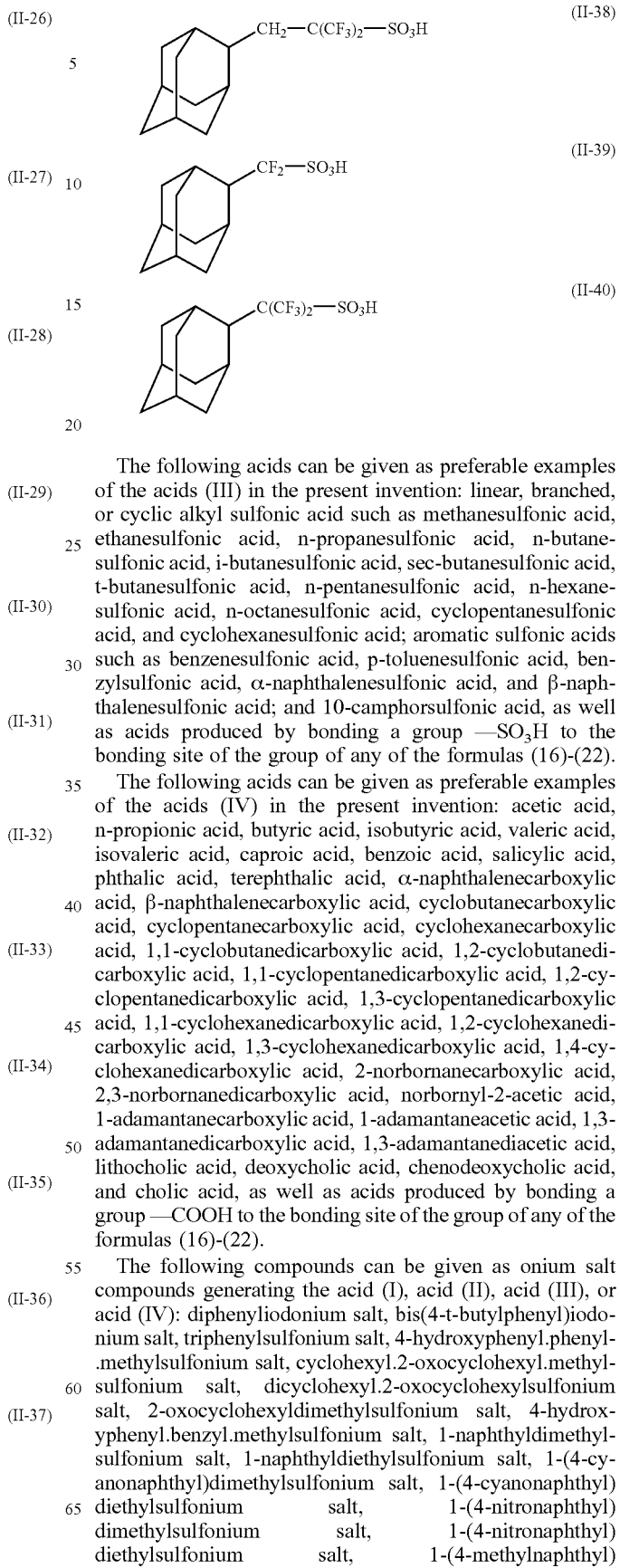

The following acids can be given as preferable examples of the acids (III) in the present invention: linear, branched, or cyclic alkyl sulfonic acid such as methanesulfonic acid, ethanesulfonic acid, n-propanesulfonic acid, n-butanesulfonic acid, i-butanesulfonic acid, sec-butanesulfonic acid, t-butanesulfonic acid, n-pentanesulfonic acid, n-hexanesulfonic acid, n-octanesulfonic acid, cyclopentanesulfonic acid, and cyclohexanesulfonic acid; aromatic sulfonic acids such as benzenesulfonic acid, p-toluenesulfonic acid, benzylsulfonic acid, α-naphthalenesulfonic acid, and β-naphthalenesulfonic acid; and 10-camphorsulfonic acid, as well as acids produced by bonding a group —SO₃H to the bonding site of the group of any of the formulas (16)-(22).

The following acids can be given as preferable examples of the acids (IV) in the present invention: acetic acid, n-propionic acid, butyric acid, isobutyric acid, valeric acid, isovaleric acid, caproic acid, benzoic acid, salicylic acid, phthalic acid, terephthalic acid, α-naphthalenecarboxylic acid, β-naphthalenecarboxylic acid, cyclobutanecarboxylic acid, cyclopentanecarboxylic acid, cyclohexanecarboxylic acid, 1,1-cyclobutanedicarboxylic acid, 1,2-cyclobutanedicarboxylic acid, 1,1-cyclopentanedicarboxylic acid, 1,2-cyclopentanedicarboxylic acid, 1,3-cyclopentanedicarboxylic acid, 1,1-cyclohexanedicarboxylic acid, 1,2-cyclohexanedicarboxylic acid, 1,3-cyclohexanedicarboxylic acid, 1,4-cyclohexanedicarboxylic acid, 2-norbornanecarboxylic acid, 2,3-norbornanedicarboxylic acid, norbornyl-2-acetic acid, 1-adamantanecarboxylic acid, 1-adamantaneacetic acid, 1,3-adamantanedicarboxylic acid, 1,3-adamantanediacetic acid, lithocholic acid, deoxycholic acid, chenodeoxycholic acid, and cholic acid, as well as acids produced by bonding a group —COOH to the bonding site of the group of any of the formulas (16)-(22).

The following compounds can be given as onium salt compounds generating the acid (I), acid (II), acid (III), or acid (IV): diphenyliodonium salt, bis(4-t-butylphenyl)iodonium salt, triphenylsulfonium salt, 4-hydroxyphenyl.phenyl.methylsulfonium salt, cyclohexyl.2-oxocyclohexyl.methylsulfonium salt, dicyclohexyl.2-oxocyclohexylsulfonium salt, 2-oxocyclohexyldimethylsulfonium salt, 4-hydroxyphenyl.benzyl.methylsulfonium salt, 1-naphthyldimethylsulfonium salt, 1-naphthyldiethylsulfonium salt, 1-(4-cyanonaphthyl)dimethylsulfonium salt, 1-(4-cyanonaphthyl) diethylsulfonium salt, 1-(4-nitronaphthyl) dimethylsulfonium salt, 1-(4-nitronaphthyl) diethylsulfonium salt, 1-(4-methylnaphthyl)

dimethylsulfonium salt, 1-(4-methylnaphthyl) diethylsulfonium salt, 1-(4-hydroxynaphthyl) dimethylsulfonium salt, 1-(4-hydroxynaphthyl) diethylsulfonium salt, 1-[1-(4-hydroxynaphthyl)] tetrahydrothiophenium salt, 1-[1-(4-ethoxynaphthyl)] tetrahydrothiophenium salt, 1-[1-(4-n-butoxynaphthyl)] tetrahydrothiophenium salt, 1-[1-(4-methoxymethoxynaphthyl)]tetrahydrothiophenium salt, 1-[1-(4-ethoxymethoxynaphthyl)]tetrahydrothiophenium salt, 1-[1-{4-(1-methoxyethoxy)naphthyl}]tetrahydrothiophenium salt, 1-[1-{4-(2-methoxyethoxy)naphthyl}] tetrahydrothiophenium salt, 1-[1-(4-methoxycarbonyloxynaphthyl)]tetrahydrothiophenium salt, 1-[1-(4-ethoxycarbonyloxynaphthyl)]tetrahydrothiophenium salt, 1-[1-(4-n-propoxycarbonyloxynaphthyl)]tetrahydrothiophenium salt, 1-[1-(4-i-propoxycarbonyloxynaphthyl)]tetrahydrothiophenium salt, 1-[1-(4-n-butoxycarbonyloxynaphthyl)]tetrahydrothiophenium salt, 1-[1-(4-t-butoxycarbonyloxynaphthyl)]tetrahydrothiophenium salt, 1-[1-{4-(2-tetrahydrofuranyloxy)naphthyl}]-tetrahydrothiophenium salt, 1-[1-{4-(2-tetrahydropyranyloxy) naphthyl}]-tetrahydrothiophenium salt, 1-[1-(4-benzyloxynaphthyl)]tetrahydrothiophenium salt, and 1-[1-(1-naphthylacetomethyl)]tetrahydrothiophenium salt.

As examples of sulfone compounds generating the acid (I), acid (II), or acid (III), β-ketosulfone, β-sulfonylsulfone, and α-diazo compounds of these compounds can be given.

As examples of sulfonic acid compounds generating the acid (I), acid (II), or acid (III), sulfonic acid esters, sulfonic acid imides, aryl sulfonic acid esters, and imino sulfonates can be given.

As examples of carboxylic acid compounds generating the acid (IV), carboxylic acid ester, carboxylic acid imide, and carboxylic acid cyanate can be given.

As examples of diazoketone compounds generating the acid (I), acid (II), acid (III), or acid (IV), 1,3-diketo-2-diazo compounds, diazobenzoquinone compounds, and diazonaphthoquinone compounds can be given.

As examples of halogen-containing compounds generating the acid (I), acid (II), acid (III), or acid (IV), haloalkyl group-containing hydrocarbon compounds, and haloalkyl group-containing heterocyclic compounds can be given.

To ensure sensitivity and developability, the amount of the acid generators (B) used in the composition of the present invention is usually 0.1-10 parts by weight, and preferably 0.5-7 parts by weight for 100 parts by weight of the acid-dissociable group-containing polysiloxane (A). If the amount of acid generator (B) is less than 0.1 part by weight, sensitivity and developability tends to decrease. If the amount exceeds 10 parts by weight, pattern configurations may be impaired due to decreased transparency to radiation.

The amount of the acid generator (B1) among the total amount of acid generators (B) is usually 10 wt % or more, preferably 20 wt % or more, and particular preferably 30-90 wt %.

In the present invention, the acid generator (B1) may be used either individually or in combination of two or more. The acid generator (B2) may also be used either individually or in combination of two or more.

Additives

Additives such as an acid diffusion controller, a dissolution controller, and a surfactant may be added to the radiation-sensitive resin composition of the present invention.

The acid diffusion controller controls the diffusion phenomenon of an acid generated from the acid generator (B) upon exposure in the resist film, thereby hindering undesired chemical reactions in the unexposed area.

The addition of such an acid diffusion controller improves storage stability of the resulting composition and resolution as a resist. Moreover, the addition of the acid diffusion controller controls changes in the line width of the resist pattern due to changes in the post-exposure delay (PED) between exposure and development, whereby a composition with remarkably superior process stability can be obtained. As the acid diffusion controller, nitrogen-containing organic compounds of which the basicity does not change due to exposure or heat treatment during formation of a resist pattern are preferable.

As examples of such nitrogen-containing organic compounds, a compound shown by the following formula (23) (hereinafter called "nitrogen-containing compound (a)"):

(23)

(wherein $R^{10}$ individually represents a hydrogen atom, a substituted or unsubstituted alkyl group, substituted or unsubstituted aryl group, or substituted or unsubstituted aralkyl group), a compound having two nitrogen atoms in the molecule (hereinafter referred to as "nitrogen-containing compound (b)"), a polymer having three or more nitrogen atoms in the molecule (hereinafter referred to as "nitrogen-containing compound (c)"), an amide group-containing compound, urea compound, and nitrogen-containing heterocyclic compound can be given.

Examples of the nitrogen-containing compounds (a) include mono(cyclo)alkylamines such as n-hexylamine, n-heptylamine, n-octylamine, n-nonylamine, n-decylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; tri(cyclo) alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, dicyclohexylmethylamine, and tricyclohexylamine; and aromatic amines such as aniline, N-methylaniline, N,N-dimethylaniline, 2-methylaniline, 3-methylaniline, 4-methylaniline, 4-nitroaniline, diphenylamine, triphenylamine, and naphthylamine.

Examples of the nitrogen-containing compounds (b) include ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

As examples of the nitrogen-containing compound (c), polyethyleneimine, polyallylamine, and a polymer of 2-dimethylaminoethylacrylamide can be given.

Examples of the amide group-containing compound include formamide, N-methylformamide, N,N-dimethylformamide, acetamide, N-methylacetamide, N,N-dimethylacetamide, propionamide, benzamide, pyrrolidone, and N-methylpyrrolidone.

As examples of the urea compound, urea, methylurea, 1,1-dimethylurea, 1,3-dimethylurea, 1,1,3,3-tetramethylurea, 1,3-diphenylurea, and tri-n-butylthiourea can be given. Examples of the nitrogen-containing heterocyclic compounds include: imidazoles such as imidazole, 4-methylimidazole, 4-methyl-2-phenylimidazole, benzimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinamide, quinoline, 4-hydroxyquinoline, 8-oxyquinoline, and acridine; piperazines such as piperazine and 1-(2-hydroxyethyl) piperazine; pyrazine, pyrazole, pyridazine, quinoxaline, purine, pyrrolidine, piperidine, morpholine, 4-methylmorpholine, 1,4-dimethylpiperazine, and 1,4-diazabicyclo [2.2.2]octane.

Of these nitrogen-containing organic compounds, the nitrogen-containing organic compounds (a) and the nitrogen-containing heterocyclic compounds are preferable. Among the nitrogen-containing organic compounds (a), tri(cyclo)alkylamines are particularly preferable. Among the nitrogen-containing heterocyclic compounds, imidazoles, pyridines, and piperazines are particularly preferable.

The acid diffusion controller may be used either individually or in combination of two or more.

The amount of the acid diffusion controller to be added is usually 15 parts by weight or less, preferably 10 parts by weight or less, and still more preferably 5 parts by weight or less for 100 parts by weight of the acid-dissociable group-containing polysiloxane (A). If the amount of the acid diffusion controller exceeds 15 parts by weight, sensitivity of the resulting resist and developability of the exposed region may be decreased. If the amount of the acid diffusion controller is less than 0.001 part by weight, the pattern shape or dimensional accuracy of the resulting resist may be decreased depending on the process conditions.

The compounds of the following formulas (24) or (25) can be given as examples of the dissolution controller.

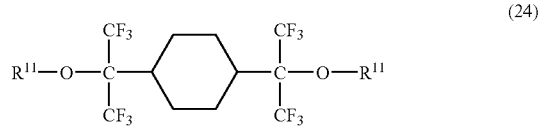

(24)

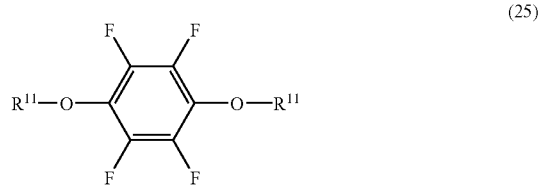

(25)

wherein $R^{11}$ individually represents a hydrogen atom, t-butyl group, t-butoxycarbonyl group, methoxymethyl group, ethoxymethyl group, 1-ethoxyethyl group, or tetrahydropyranyl group.

The amount of the dissolution controller to be added is usually 2-30 parts by weight, and preferably 5-20 parts by weight, for 100 parts by weight of the acid-dissociable group-containing polysiloxane.

Surfactants improve applicability, developability, and the like of the radiation-sensitive resin composition.

As examples of the surfactant, nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate; and commercially available products such as KP341 (manufactured by Shin-Etsu Chemical Co., Ltd.), Polyflow No. 75, No. 95 (manufactured by Kyoeisha Chemical Co., Ltd.), FTOP EF301, EF303, EF352 (manufactured by Tohkem Products Corporation), MEGAFAC F171, F173 (manufactured by Dainippon Ink and Chemicals, Inc.), Fluorard FC430, FC431 (manufactured by Sumitomo 3M Ltd.), Asahi Guard AG710, and Surflon S-382, SC-101, SC-102, SC-103, SC-104, SC-105, SC-106 (manufactured by Asahi Glass Co., Ltd.) can be given.

The surfactant may be used either individually or in combination of two or more.

The amount of surfactants to be added is usually 2 parts by weight or less for 100 parts by weight of the total of the acid-dissociable group-containing polysiloxane and the acid generator (B).

As other additives, halation inhibitors, adhesion promoters, storage stabilizers, anti-foaming agents, and the like can be given.

The radiation-sensitive resin composition of the present invention is usually prepared as a composition solution by dissolving the components in a solvent and filtering the solution through a filter with a pore size of about 0.2 μm.

Any solvent capable of dissolving the acid-dissociable group-containing polysiloxanes, acid generators, and additives can be used for the composition solution without any specific limitation. Examples of the solvents that can be used include: linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, and 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl 2-hydroxypropionates such as methyl 2-hydroxypropionate, ethyl 2-hydroxypropionate, n-propyl 2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; and alkyl 3-alkoxypropionates such as methyl 3-methoxypropionate, ethyl 3-methoxypropionate, methyl 3-ethoxypropionate, and ethyl 3-ethoxypropionate; as well as other solvents such as n-propyl alcohol, i-propyl alcohol, n-butyl alcohol, t-butyl alcohol, cyclohexanol, ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether, propylene glycol monoethyl ether, propylene glycol mono-n-propyl ether, toluene, xylene, ethyl 2-hydroxy-2-methyl propionate, ethoxyethyl acetate, ethyl hydroxyacetate, methyl 2-hydroxy-3-methylbutyrate, 3-methoxybutylacetate, 3-methyl-3-methoxybutylacetate, 3-methyl-3-methoxybutylpropionate, 3-methyl-3-methoxybutylbutyrate, ethyl acetate, n-propyl acetate, n-butyl acetate, methyl acetoacetate, ethyl acetoacetate, methylpyruvate, ethyl pyruvate, N-methyl pyrrolidone, N,N-dimethylformamide, N,N-dimethylacetamide, benzyl ethyl ether, di-n-hexyl ether, diethylene glycol monomethyl ether, diethylene glycol monoethyl ether, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, and propylene carbonate.

These solvents may be used either individually or in combination of two or more. Among these solvents, linear or branched ketones, cyclic ketones, propylene glycol monoalkyl ether acetates, alkyl 2-hydroxypropionates, and alkyl 3-alkoxypropionates are preferable.

The solvent is used in the liquid composition of the radiation-sensitive resin composition in an amount to make the total solid content of the solution usually 1-25 wt %, and preferably 2-15 wt %.

The radiation-sensitive resin composition of the present invention is particularly suitable for use as a chemically-amplified resist for forming resist patterns on substrates.

Under Layer Film

When forming the resist pattern using the radiation-sensitive resin composition of the present invention, a under layer film may be previously formed on the substrate to suppress the effect of stationary waves due to radiation.

As the polymer forming under layer film (hereinafter referred to as "under layer film polymer"), a polymer capable of efficiently suppressing the effect of stationary waves and possessing sufficient dry etching resistance is preferable. In particular, polymers having a carbon content of preferably 85 wt % or more, and more preferably 90 wt % or more, and containing an aromatic hydrocarbon structure in the molecule is preferable (such a polymer is hereinafter referred to as "under layer film polymer (β)").

As the under layer film polymer (β), polymers having the structural unit of the following formula (26) (hereinafter referred to as "under layer film polymer (β-1)"), polymers having the structural unit of the following formula (27) (hereinafter referred to as "under layer film polymer (β-2)") polymers having the structural unit of the following formula (28) (hereinafter referred to as "under layer film polymer (β-3)"), polymers having the structural unit of the following formula (29) (hereinafter referred to as "under layer film polymer (β-4)"), and the like can be given.

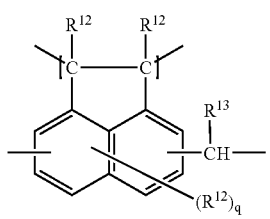

(26)

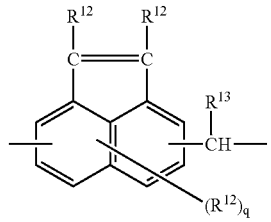

(27)

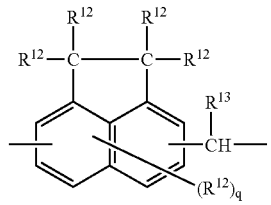

(28)

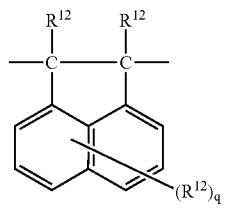

(29)

wherein $R^{12}$ individually represents a monovalent atom or a monovalent group, q is an integer of 0-4, and $R^{13}$ is a hydrogen atom or a monovalent organic group.

As examples of the monovalent atom or monovalent group represented by $R^{12}$ in the formulas (26) to (29), a halogen atom, hydroxyl group, mercapto group, carboxyl group, nitro group, sulfonic acid group, phenyl group, alkyl group, alkenyl group, amino group, and acyl group can be given, wherein one or more hydrogen atoms on the phenyl group, alkyl group, and alkenyl group may be replaced by one or more, same or different, substituents such as a halogen atom, hydroxyl group, mercapto group, carboxyl group, nitro group, and sulfonic acid group.

As examples of the halogen atom, a fluorine atom, chlorine atom, and bromine atom can be given.

As the alkyl group, alkyl groups having 1-10 carbon atoms are preferable. Particularly preferable examples are linear or branched alkyl groups having 1-6 carbon atoms, such as a methyl group, ethyl group, n-propyl group, i-propyl group, n-butyl group, i-butyl group, sec-butyl group, and t-butyl group.

As the alkenyl group, alkenyl groups having 2-10 carbon atoms are preferable. Particularly preferable examples are linear or branched alkenyl groups having 2-6 carbon atoms, such as a vinyl group, propenyl group, 1-butenyl group, and 2-butenyl group.

As the amino group, primary amino groups are preferable. Particularly preferable examples are linear or branched primary amino groups having 1-6 carbon atoms, such as an aminomethyl group, 2-aminoethyl group, 3-aminopropyl group, and 4-aminobutyl group.

As the acyl group, acyl groups having 2-10 carbon atoms are preferable. Particularly preferable examples are aliphatic or aromatic acyl groups having 2-6 carbon atoms, such as an acetyl group, propionyl group, butyryl group, and benzoyl group.

As examples of the monovalent organic group represented by $R^{13}$, alkyl groups, alkenyl groups, alicyclic groups, aromatic hydrocarbon groups, and heterocyclic groups can be given.

As the alkyl groups, linear or branched alkyl groups having 1-6 carbon atoms, such as a methyl group, ethyl group, n-propyl group, i-propyl group, n-butyl group, i-butyl group, sec-butyl group, and t-butyl group are preferable.

As the alkenyl groups, linear or branched alkenyl groups having 2-6 carbon atoms such as a vinyl group, propenyl group, 1-butenyl group, and 2-butenyl group are preferable. As the alicyclic groups, alicyclic groups having 4-10 carbon atoms such as a cyclopentyl group and cyclohexyl group are preferable.

As the aromatic hydrocarbon groups, aromatic hydrocarbon groups having 6-12 carbon atoms such as a phenyl group, 1-naphthyl group, and 2-naphthyl group are preferable.

As the heterocyclic groups, 4-10 member heterocyclic groups such as a 2-furanyl group, tetrahydro-2-furanyl group, furfuryl group, tetrahydrofurfuryl group, thiofurfuryl group, 2-pyranyl group, tetrahydro-2-pyranyl group, 2-pyranylmethyl group, and tetrahydro-2-pyranylmethyl group are preferable.

The under layer film polymers (β) can be prepared by the following methods, for example. However, the process of preparing the under layer film polymers (β) are not limited to these methods.

Preparation Method (a)

(a-1) A method of condensing an acenaphthylene and an aldehyde, optionally, together with other co-condensable aromatic compounds in the presence of an acid catalyst to obtain a polymer, followed by polymerizing this polymer, either independently or in combination with other copolymerizable monomers; or (a-2) a method of polymerizing an acenaphthylene, either independently or in combination with other copolymerizable monomers, and condensing the resulting polymer with an aldehyde, optionally, together with other co-condensable aromatic compounds in the presence of an acid catalyst to obtain a under layer film polymer (β-1).

Preparation Method (b)

A method of condensing an acenaphthylene and an aldehyde, optionally, together with other co-condensable aromatic compounds in the presence of an acid catalyst to obtain the under layer film polymer (β-2).

Preparation Method (c)

A method of condensing an acenaphthene and an aldehyde, optionally, together with other co-condensable aromatic compounds in the presence of an acid catalyst to obtain the under layer film polymer (β-3).

The under layer film polymer (β-4) can be obtained by the step of polymerizing an acenaphthylene, either independently or in combination with other copolymerizable monomers, in the method of (a-2).

The polymerization in the preparation method (a) may be carried out by radical polymerization, anionic polymerization, cationic polymerization, or the like using an appropriate process such as mass polymerization process, solution polymerization process, or the like.

Mw of the polymer obtained by condensing an acenaphthylene and an aldehyde, optionally, together with other co-condensable aromatic compounds in the preparation method (a-1) and Mw of the polymer obtained by polymerizing an acenaphthylene, either independently or in combination with other copolymerizable monomers in the preparation method (a-2) can be appropriately selected usually in the range of 100-10,000, and preferably of 2,000-5,000, according to the characteristics desired for the under layer film.

The condensation reaction of the preparation methods (a)-(c) is carried out in the presence of an acid catalyst, either using or not using a solvent (preferably using a solvent), by heating the reaction mixture.

As the acid catalyst, mineral acids such as sulfuric acid, phosphoric acid, and perchloric acid; organic sulfonic acids such as p-toluenesulfonic acid, carboxylic acids such as formic acid and oxalic acid, the like can be given.

The amount of the acid catalysts used is appropriately adjusted according to the type of acids used. Such an amount is usually 0.001-10,000 parts by weight, preferably 0.01-1,000 parts by weight, for 100 parts by weight of the acenaphthylenes or acenaphthenes.

The solvents used for the condensation reaction in the preparation methods (a)-(c) are not specifically limited inasmuch as the solvents do not interfere with the condensation reaction. For example, solvents conventionally used for the synthesis of resins in which an aldehyde compound is used as a raw material, such as phenol resins, melamine resins, and amino-type resins, can be used. Specific examples include, in addition to the previously described solvents for preparing the composition solutions of the radiation-sensitive resin composition of the present invention, cyclic ethers such as tetrahydrofuran and dioxane. When the acid catalyst used is liquid such as formic acid, for example, the acid catalyst may also function as a solvent.

These solvents may be used either individually or in combinations of two or more.

The reaction temperature in the condensation reaction in the preparation methods (a)-(c) is usually from 40° C. to 200° C. The reaction time is appropriately adjusted according to the reaction temperature usually in the range of 30 minutes to 72 hours.

Mw of the under layer film polymer (β) is usually 500-100,000, and preferably 5,000-50,000.

The under layer film polymer (β) may be used either individually or in combination of two or more.

When forming the under layer films using the under layer film polymer, a solution in which the under layer film polymer is dissolved in a solvent, optionally together with additives that are described later, is used. Such a solution is hereinafter referred to as "composition solution for forming under layer films."

Any solvent capable of dissolving the under layer film polymers and additives can be used without any specific limitation for the composition solution for forming under layer films. Examples of the solvents that can be used include: ethylene glycol monoalkyl ethers such as ethylene glycol monomethyl ether, ethylene glycol monoethyl ether, ethylene glycol mono-n-propyl ether, and ethylene glycol mono-n-butyl ether; ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; diethylene glycol dialkyl ethers such as diethylene glycol dimethyl ether, diethylene glycol diethyl ether, diethylene glycol di-n-propyl ether, diethylene glycol di-n-butyl ether; propylene glycol monoalkyl ethers such as propylene glycol monbmethyl ether, propylene glycol monoethyl ether, propylene glycol mono-n-propyl ether, and propylene glycol mono-n-butyl ether; propylene glycol dialkyl ethers such as propylene glycol dimethyl ether, propylene glycol diethyl ether, propylene glycol di-n-propyl ether, and propylene glycol di-n-butyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; lactic acid esters such as methyl lactate, ethyl lactate, n-propyl lactate, i-propyl lactate, n-butyl lactate, and i-butyl lactate; aliphatic carboxylic acid esters such as methyl formate, ethyl formate, n-propyl formate, i-propyl formate, n-butyl formate, i-butyl formate, n-amyl formate, i-amyl formate, methyl acetate, ethyl acetate, n-propyl acetate, i-propyl acetate, n-butyl acetate, i-butyl acetate, n-amyl acetate, i-amyl acetate, n-hexyl acetate, methyl propionate, ethyl propionate, n-propyl propionate, i-propyl propionate, n-butyl propionate, i-butyl propionate, methyl butyrate, ethyl butyrate, n-propyl butyrate, i-propyl butyrate, n-butyl butyrate, and i-butyl butyrate; other esters such as ethyl hydroxyacetate, ethyl 2-hydroxy-2-methylpropionate, methyl 3-methoxy-2-methylpropionate, methyl 2-hydroxy-3-methylbutyrate, ethyl methoxyacetate, ethyl ethoxyacetate, methyl 3-methoxypropionate, ethyl 3-methoxypropionate, methyl 3-ethoxypropionate, ethyl 3-ethoxypropionate, propyl 3-methoxyacetate, butyl 3-methoxyacetate, butyl 3-methyl-3-methoxyacetate, butyl 3-methyl-3-methoxypropionate, butyl 3-methyl-3-methoxybutyrate, methyl acetoacetate, methyl pyruvate, and ethyl pyruvate; aromatic hydrocarbons such as toluene and xylene; ketones such as methyl ethyl ketone, 2-pentanone, 2-hexanone, 2-heptanone, 3-heptanone, 4-heptanone, and cyclohexanone; amides such as N-methylformamide, N,N-dimethylformamide, N-methylacetamide, N,N-dimethyl acetamide, and N-methylpyrrolidone; and lactones such as γ-butyrolactone can be given.

Of these solvents, ethylene glycol monoethyl ether acetates, ethyl lactate, methyl 3-methoxypropionate, ethyl 3-ethoxypropionate, 2-heptanone, cyclohexanone, and the like are preferable.

These solvents may be used either individually or in combination of two or more.

The solvent is used in the composition solution for forming the under layer films in an amount to make the total solid content in the solution usually 0.01-70 wt %, preferably 0.05-60 wt %, and more preferably 0.1-50 wt %.

Various additives such as crosslinking agents, polymers other than the under layer film polymers, radiation absorbents, surfactants, acid generators, preservatives, anti-foaming agents, and adhesion adjuvants can be added to the composition solution for forming under layer films as required.

The composition solution for forming under layer films is usually filtered through a filter with a pore size of about 0.1 μm before using for forming under layer films.

Formation of Resist Patterns

As a method for forming a resist pattern using the radiation-sensitive resin composition of the present invention, a method comprising: 1) a step of forming an under layer film on a substrate by applying the composition solution for forming under layer films onto the substrate and baking the coating, 2) a step of forming a coating by applying the solution of the radiation-sensitive resin composition onto the under layer film and pre-baking the resulting coating (hereinafter referred to as "resist film"), 3) a step of exposing selected areas of the resist film to radiation through a mask for exposure, 4) a step of developing the exposed resist film to form a resist pattern, and, if required, 5) a step of etching the under layer film using the resist pattern as a mask can be given.

This method will now be described in more detail.

There is no specific limitation to the substrate used for forming a resist pattern. Inorganic substrates such as a silicon-type oxide film and interlayer dielectric film can be given as examples.

In the step 1), after applying the composition solution for forming under layer films on the substrate by an appropriate means such as rotation coating, cast coating, or roll coating, for example, the resulting coating is baked to volatilize the solvent, thereby forming the under layer film.

The baking temperature is usually from 90 to 500° C., and preferably from 200 to 450° C.

The thickness of the under layer film is usually 10-10,000 nm, and preferably 50-1,000 nm.

In the step 2), the resist film having a specific thickness is formed by applying the solution of the radiation-sensitive resin composition of the present invention on the under layer film using an appropriate means such as rotation coating, cast coating, or roll coating, for example, and prebaking the resulting coating to volatilize the solvent.

In this instance, a prebaking temperature is appropriately adjusted according to the radiation-sensitive resin composition used and the like in the range usually from 30 to 200° C., and preferably from 50 to 160° C.

The thickness of the resist film is usually 10-10,000 nm, preferably 50-1,000 nm, and particularly preferably 70-300 nm.

Next, in the step 3), the resist film is selectively exposed to radiation through a mask for exposure.

As radiation used for exposure, visible rays, ultraviolet rays, deep ultraviolet rays, X-rays, electron beams, γ-rays, molecular beams, ion beams, or the like are appropriately selected depending on the radiation-sensitive resin composition used. It is particularly preferable to use deep ultraviolet rays such as a KrF excimer laser (wavelength: 248 nm), ArF excimer laser (wavelength: 193 nm), F2 excimer laser (wavelength: 157 nm), and extreme ultraviolet rays (EUV) or electron beams. The ArF excimer laser and F2 excimer laser are ideal deep ultraviolet rays.

Next, in the step 4), the resist film after exposure is developed to form a resist pattern.

As examples of a developer used for development, alkaline aqueous solutions prepared by dissolving alkaline compounds such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo-[5.4.0]-7-undecene, and 1,5-diazabicyclo-[4.3.0]-5-nonene can given.

An appropriate amount of a water-soluble organic solvent such as alcohols including methanol and ethanol or surfactants can be added to these alkaline aqueous solutions.

The resist film is then washed with water and dried to obtain a desired resist pattern.

In this step, post-baking may be carried out before development to improve resolution, pattern forms, developability, and the like.

In this instance, a post-baking temperature is appropriately adjusted according to the radiation-sensitive resin composition used and the like usually in the range of 30 to 200° C., and preferably of 50 to 160° C.

In the step 5), if required, the under layer film is etched using the obtained resist pattern as a mask and gas plasmas such as fluorine plasma, chlorine plasma, or bromine plasma to obtain a desired pattern.

However, the method of forming a resist pattern in the present invention is not limited to the above-described methods.

EXAMPLES

The present invention will be described in detail below. However, the present invention is not limited to these following examples.

Synthesis Example 1

Synthesis of Polysiloxane (α)

A three-necked flask equipped with a stirrer, a reflux condenser, and a thermometer was charged with 8.34 g of the compound of the following formula (30), 12.92 g of the compound of the following formula (31), 8.75 g of methyltriethoxysilane, 30 g of 4-methyl-2-pentanone, and 7.20 g of a 1.75 wt % aqueous solution of oxalic acid. The mixture was reacted for 6 hours at 80° C. while stirring, followed by cooling with ice to terminate the reaction. The reaction solution was poured into a separating funnel to remove the water layer. The organic layer was repeatedly washed with ion-exchanged water until the reaction solution became neutral. The solvent was evaporated under reduced pressure from the organic layer to obtain 18.5 g of a polysiloxane (α).

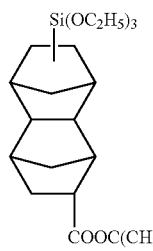

(30)

wherein the silicon atom bonds to the 3-position or 4-position of the tetracyclo[4.4.0.1$^{2,5}$.1$^{7,10}$]dodecane ring.

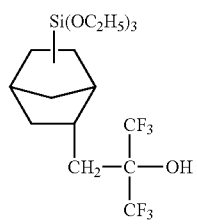

(31)

wherein the silicon atom bonds to the 2-position or 3-position of the bicyclo[2.2.1]heptane ring.

$^1$H-NMR spectrum (chemical shift σ), Mw, and Mn of the polysiloxane (α) were measured. The results were as follows.

σ: 2.3 ppm (CH$_2$C(CF$_3$)$_2$ group), 1.4 ppm (t-butyl group), 0.2 ppm (SiCH$_3$ group)
Mw: 2,300
Mw/Mn: 1.1

This polysiloxane (α) is designated as "polysiloxane (α-1)."

Synthesis Example 2

Synthesis of Polysiloxane (α)

A three-necked flask equipped with a stirrer, a reflux condenser, and a thermometer was charged with 3.84 g of the compound of the above formula (30), 7.93 g of the compound of the above formula (31), 3.22 g of methyltriethoxysilane, 15 g of 4-methyl-2-pentanone, and 3.32 g of a 1.75 wt % aqueous solution of oxalic acid. The mixture was reacted for 6 hours at 80° C. while stirring, followed by cooling with ice to terminate the reaction. The reaction solution was poured into a separating funnel to remove the water layer. The organic layer was repeatedly washed with ion-exchanged water until the reaction solution became neutral. The solvent was evaporated under reduced pressure from the organic layer to obtain 8.24 g of a polysiloxane (α).

$^1$H-NMR spectrum (chemical shift σ), Mw, and Mn of the polysiloxane (α) were measured. The results were as follows.

σ: 2.3 ppm (CH$_2$C(CF$_3$)$_2$ group), 1.4 ppm (t-butyl group), 0.2 ppm (SiCH$_3$ group)
Mw: 2,200
Mw/Mn: 1.1

This polysiloxane (α) is designated as "polysiloxane (α-2)."

Synthesis Example 3

Synthesis of Polysiloxane (α)

A three-necked flask equipped with a stirrer, a reflux condenser, and a thermometer was charged with 1.90 g of the compound of the above formula (30), 6.89 g of the compound of the above formula (31), 1.21 g of methyltriethoxysilane, 10 g of 4-methyl-2-pentanone, and 1.65 g of a 1.75 wt % aqueous solution of oxalic acid. The mixture was reacted for 10 hours at 40° C. while stirring, followed by cooling with ice to terminate the reaction. The reaction solution was poured into a separating funnel to remove the water layer. The organic layer was repeatedly washed with ion-exchanged water until the reaction solution became neutral. The solvent was evaporated under reduced pressure from the organic layer to obtain 7.5 g of a viscous oily resin. The resin had an Mw of 1,500 and an Mw/Mn ratio of 1.1.

The resin was dissolved in 22.5 g of 4-methyl-2-pentanone. After the addition of 2.43 g of distilled water and 3.40 g of triethylamine, the mixture was heated to 60° C. in a nitrogen stream. After five hours, the reaction solution was cooled with ice while stirring, then a solution of 2.83 g of oxalic acid in 70 g of distilled water was added, followed by further stirring. The reaction solution was poured into a separating funnel to remove the water layer. The organic layer was repeatedly washed with ion-exchanged water until the reaction solution became neutral. The solvent was evaporated under reduced pressure from the organic layer to obtain 7.38 g of a polysiloxane (α).

$^1$H-NMR spectrum (chemical shift σ), IR spectrum, Mw, and Mn of the polysiloxane (α) were measured. The results were as follows.

σ: 2.3 ppm (CH$_2$C(CF$_3$)$_2$ group), 1.5 ppm (t-butoxycarbonyl group), 1.4 ppm (t-butoxy group)
IR: 1775 cm$^{-1}$ (carbonate group), 1726 cm$^{-1}$ (ester group), 1221 cm$^{-1}$ (C—F bond), 1133 cm$^{-1}$ (siloxane group)
Mw: 2,300
Mw/Mn: 1.1

This polysiloxane (α) is designated as "polysiloxane (α-3)."

Synthesis Example 4

Synthesis of Polysiloxane (α)

A three-necked flask equipped with a stirrer, a reflux condenser, and a thermometer was charged with 2.79 g of the compound of the above formula (31), 1.14 g of methyltriethoxysilane, 1.07 g of the compound of the following formula (32), 5.0 g of 4-methyl-2-pentanone, and 0.78 g of a 1.75 wt % aqueous solution of oxalic acid. The mixture was reacted for 10 hours at 40° C. while stirring, followed by cooling with ice to terminate the reaction. The reaction solution was poured into a separating funnel to remove the water layer. The organic layer was repeatedly washed with ion-exchanged water until the reaction solution became neutral. The solvent was evaporated under reduced pressure from the organic layer to obtain 3.6 g of a viscous oily resin. The resin had an Mw of 1,600 and an Mw/Mn ratio of 1.1.

The resin was dissolved in 11.4 g of 4-methyl-2-pentanone. After the addition of 1.15 g of distilled water and 1.61 g of triethylamine, the mixture was heated to 60° C. in a nitrogen stream. After five hours, the reaction solution was cooled with ice while stirring, then absolution of 1.34 g of oxalic acid in 50 g of distilled water was added, followed by further stirring. The reaction solution was poured into a separating funnel to remove the water layer. The organic layer was repeatedly washed with ion-exchanged water until the reaction solution became neutral. The solvent was evaporated under reduced pressure from the organic layer to obtain 3.23 g of a polysiloxane (α).

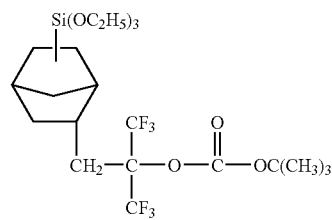

(32)

wherein the silicon atom bonds to the 2-position or 3-position of the bicyclo[2.2.1]heptane ring.

$^1$H-NMR spectrum (chemical shift σ), IR spectrum, Mw, and Mn of the polysiloxane (α) were measured. The results were as follows.

σ: 2.3 ppm (CH$_2$C(CF$_3$)$_2$ group), 1.5 ppm (t-butoxycarbonyl group)
IR: 1775 cm$^{-1}$ (carbonate group), 1221 cm$^{-1}$ (C—F bond), 1130 cm$^{-1}$ (siloxane group)
Mw: 2,500
Mw/Mn: 1.1

This polysiloxane (α) is designated as "polysiloxane (α-4)."

Synthesis Example 5

Synthesis of Under Layer Film-forming Polymer (β)

A separable flask equipped with a thermometer was charged with 100 parts by weight of acenaphthylene, 78 parts by weight of toluene, 52 parts by weight of dioxane, and 3 parts by weight of azobisisobutyronitrile in a nitrogen atmosphere. The mixture was stirred for 5 hours at 70° C. Next, 5.2 parts by weight of p-toluenesulfonic acid monohydrate and 40 parts by weight of paraformaldehyde were added. After heating to 120° C., the mixture was stirred for 6 hours. The reaction solution was charged into a large amount of isopropanol. The resulting precipitate was collected by filtration and dried at 40° C. under reduced pressure to obtain a under layer film-forming polymer (β).

Mw of the under layer film-forming polymer (β) was found to be 22,000 and $^1$H-NMR analysis confirmed that the polymer has the structural unit of the following formula (33).

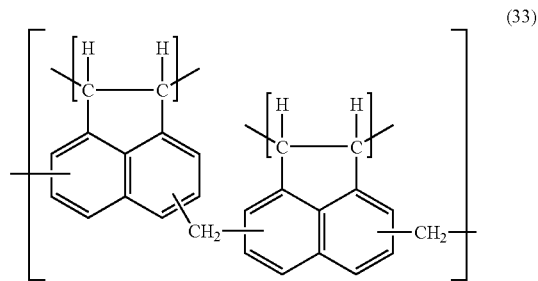

(33)

This under layer film-forming polymer (β) is referred to as a "under layer film-forming polymer (β-1)."

Synthesis Example 6

Synthesis of Acid Generator (B1)

An eggplant-shaped flask was charged with a solution of 20 g of triphenylsulfonium chloride in 500 ml of water. A separately prepared solution of 20 g of sodium 1,1,2,2-tetrafluoro-2-(norbornan-2-yl)ethanesulfonate in 500 ml of water was added dropwise to the solution at room temperature. The mixture was stirred for 30 minutes. The reaction solution was extracted with ethyl acetate. The organic layer was washed with water twice and distilled under reduced pressure to obtain colorless highly viscous oil of triphenylsulfonium 1,1,2,2-tetrafluoro-2-(norbornan-2-yl)ethanesulfonate of the following formula (34) (yield 43%).

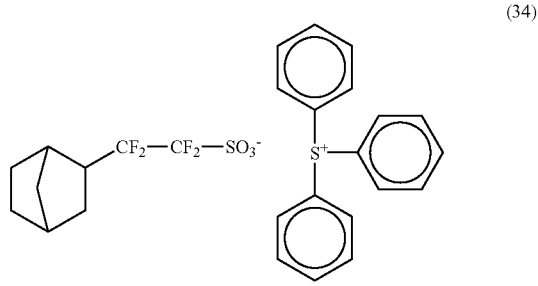

(34)

Preparation Example 1

10 parts by weight of the under layer film-forming polymer (β-1) prepared in Synthesis Example 5, 0.5 part by weight of bis(4-t-butylphenyl)iodonium 10-camphorsulfonate, and 0.5 part by weight of 4,4'-[1-{4-(1-[4-hydroxyphenyl]-1-methylethyl)phenyl}ethylidene]bisphenol were dissolved in 89 parts by weight of cyclohexanone to prepare a homogeneous solution. The solution was filtered using a membrane filter with a pore diameter of 0.1 μm to prepare a composition solution for under layer film-forming polymer (hereinafter referred to as "composition solution (β-0.1)")

Evaluation Example 1

Resolution by Exposure to ArF Excimer Laser

Composition solutions were prepared by homogeneously mixing a polysiloxane (α) in Table 1-1 or 1-2 and 900 parts by weight of 2-heptanone with the acid generator (B-1), acid generator (B-2), and acid diffusion controller in Table 1-1 or 1-2.

The composition solutions were applied onto a silicon wafer substrate (Si), a silicon wafer substrate on which the underlayer film (β-1) was previously formed, or a silicon wafer substrate on which the under layer film (1) was previously formed, by spin coating and pre-baked for 90 seconds on a hot plate at 140° C. (Comparative Example 1 and Examples 1-15) or on a hot plate at 100° C. (Examples 16-17) to form a resist film with a thickness of 100 nm.

The under layer film (β-1) was prepared by coating the composition solution (β-1) so that a film with a thickness of 3,000 Å can be obtained, followed by baking for 60 seconds at 180° C. and for 120 seconds at 300° C. The under layer film (1) was formed by coating a commercially available antireflection film DUV-30J (thickness: 520 Å), followed by baking for 60 seconds at 205° C. The resist films were exposed to an ArF excimer laser (wavelength: 193 nm, NA=0.60, and σ=0.70) while changing the irradiation dose, post-baked for 90 seconds on a hot plate maintained at 110° C. in Comparative Example 1 and Examples 1-15 or at 100° C. in Examples 16-17, and then developed in a 2.38 wt % aqueous solution of tetramethylammonium hydroxide, thereby forming a line-and-space pattern (1L/1S).

The evaluation results are shown in Tables 1-1 and 1-2.
Components in Tables 1-1 and 1-2 other than the polysiloxanes are as follows.

Acid Generator (B1)
  B1-1: Triphenylsulfonium trifluoromethanesulfonate
  B1-2: Triphenylsulfonium nonafluoro-n-butanesulfonate
  B1-3: Triphenylsulfonium perfluoro-n-octanesulfonate
  B1-4: Diphenyliodonium nonafluoro-n-butanesulfonate
  B1-5: Compound of the formula (34)

Acid Generator (B2)
  B2-1: Triphenylsulfonium 10-camphorsulfonate
  B2-2: Diphenyliodonium 10-camphorsulfonate
  B2-3: Triphenylsulfonium salicylate Acid Diffusion Controller
  C-1: Tri-N-octylamine
  C-2: 2-Phenylbenzimidazole
  C-3: 4-Phenylpyridine

TABLE 1

| | Polysiloxane (a) (parts by weight) | Substrate | Acid generator (parts by weight) B1 | B2 | Acid diffusion controller (mol %) (*) | Resolution |
|---|---|---|---|---|---|---|
| Comparative Example 1 | α-1 (50) α-2 (50) | Si | — | B2-1 (1) | C-1 (8) | (**) |
| Example 1 | α-1 (50) α-2 (50) | Si | B1-1 (1) | B2-1 (1) | C-1 (8) | (**) |
| Example 2 | α-1 (50) α-2 (50) | Si | B1-1 (1) | B2-1 (1) | C-1 (8) | 0.14 |
| Example 3 | α-1 (50) α-2 (50) | Under layer film (1) | B1-2 (1) | B2-1 (1) | C-1 (8) | 0.14 |
| Example 4 | α-1 (50) α-2 (50) | Under layer film (1) | B1-2 (1) | B2-1 (0.5) | C-1 (8) | 0.14 |
| Example 5 | α-1 (50) α-2 (50) | Under layer film (1) | B1-2 (1) | B2-1 (0.5) | C-2 (8) | 0.14 |
| Example 6 | α-1 (50) α-2 (50) | Under layer film (1) | B1-2 (1) | B2-1 (0.5) | C-3 (8) | 0.14 |
| Example 7 | α-1 (50) α-2 (50) | Under layer film (1) | B1-2 (3) | B2-1 (0.5) | C-3 (8) | 0.14 |
| Example 8 | α-1 (50) α-2 (50) | Under layer film (1) | B1-4 (3) | B2-2 (0.5) | C-3 (8) | 0.14 |
| Example 9 | α-1 (50) α-2 (50) | Under layer film (1) | B1-3 (1) | B2-1 (0.5) | C-3 (8) | 0.14 |
| Example 10 | α-1 (50) α-2 (50) | Under layer film (1) | B1-2 (3) | B2-3 (0.5) | C-3 (8) | 0.14 |
| Example 11 | α-1 (50) α-2 (50) | Under layer film (β-1) | B1-1 (1) | B2-1 (0.5) | C-3 (8) | 0.14 |
| Example 12 | α-1 (50) α-2 (50) | Si | B1-5 (1) | — | C-1 (8) | 0.15 |
| Example 13 | α-1 (50) α-2 (50) | Si | B1-5 (1) | — | C-1 (8) | 0.14 |

TABLE 1-continued

|  | Polysiloxane (a) (parts by weight) | Substrate | Acid generator (parts by weight) B1 | B2 | Acid diffusion controller (mol %) (*) | Resolution |
|---|---|---|---|---|---|---|
| Example 14 | α-1 (50)<br>α-2 (50) | Si | B1-5 (1) | B2-1 (0.5) | C-1 (8) | 0.14 |
| Example 15 | α-1 (50)<br>α-2 (50) | Under layer film (1) | B1-5 (1) | B2-2 (0.5) | C-1 (8) | 0.14 |
| Example 16 | α-3 (100) | Under layer film (1) | B1-2 (1) | B2-1 (0.5) | C-3 (8) | 0.14 |
| Example 17 | α-4 (100) | Under layer film (1) | B1-2 (1) | B2-3 (0.5) | C-3 (8) | 0.14 |

*Mol % per total amount of the acid generator (B) (hereinafter the same).
**Patterns could not be formed.

Evaluation Example 2

Resolution by Exposure to F2 Excimer Laser

Composition solutions were prepared by homogeneously mixing polysiloxane (α) in Table 2 and 900 parts by weight of 2-heptanone with the acid generator (B-1), acid generator (B-2), and acid diffusion controller shown in Table 2.

The composition solutions were applied onto a silicon wafer substrate (Si), a silicon wafer substrate on which the under layer film (β-1) was previously formed, or a silicon wafer substrate on which the under layer film (1) was previously formed, by spin coating and pre-baked for 90 seconds on a hot plate at 140° C. (Examples 18-27) or on a hot plate at 100° C. (Examples 28-31) to form a resist film with a thickness of 100 nm.

Using a binary mask as a reticle, the resist films were exposed to an F2 excimer laser (wavelength: 157 nm, NA=0.60, and σ=0.70) while changing the irradiation dose, post-baked for 90 seconds on a hot plate maintained at 110° C. (Examples 18-27) or at 100° C. (Examples 28-31), and then developed in a 2.38 wt % aqueous solution of tetramethylammonium hydroxide, thereby forming a line-and-space pattern (1L/1S).

The evaluation results are shown in Table 2.

Components in Table 2 other than the polysiloxanes (α) are as described above.

TABLE 2

|  | Polysiloxane (a) (parts by weight) | Substrate | Acid generator (parts by weight) B1 | B2 | Acid diffusion controller (mol %) (*) | Resolution |
|---|---|---|---|---|---|---|
| Example 18 | α-1 (50)<br>α-2 (50) | Si | B1-1 (1) | B2-1 (0.5) | C-1 (8) | 0.09 |
| Example 19 | α-1 (50)<br>α-2 (50) | Si | B1-2 (1) | B2-1 (0.5) | C-1 (8) | 0.09 |
| Example 20 | α-1 (50)<br>α-2 (50) | Si | B1-2 (1) | B2-1 (0.5) | C-3 (8) | 0.09 |
| Example 21 | α-1 (50)<br>α-2 (50) | Under layer film (1) | B1-2 (1) | B2-1 (0.5) | C-3 (8) | 0.09 |
| Example 22 | α-1 (50)<br>α-2 (50) | Under layer film (1) | B1-2 (1) | B2-1 (0.5) | C-2 (8) | 0.09 |
| Example 23 | α-1 (50)<br>α-2 (50) | Under layer film (1) | B1-2 (1) | B2-1 (0.5) | C-3 (8) | 0.09 |
| Example 24 | α-1 (50)<br>α-2 (50) | Under layer film (1) | B1-2 (1) | B2-1 (0.5) | C-3 (8) | 0.09 |
| Example 25 | α-1 (50)<br>α-2 (50) | Under layer film (β-1) | B1-5 (1) | B2-1 (0.5) | C-3 (8) | 0.09 |
| Example 26 | α-1 (50)<br>α-2 (50) | Under layer film (1) | B1-5 (1) | — | C-1 (8) | 0.10 |
| Example 27 | α-1 (50)<br>α-2 (50) | Under layer film (1) | B1-5 (1) | B2-1 (0.5) | C-1 (8) | 0.09 |
| Example 28 | α-3 (100) | Under layer film (1) | B1-2 (1) | B2-1 (0.5) | C-3 (8) | 0.09 |
| Example 29 | α-4 (100) | Under layer film (1) | B1-2 (1) | B2-1 (0.5) | C-3 (8) | 0.09 |
| Example 30 | α-3 (100) | Under layer film (β-1) | B1-2 (1) | B2-1 (0.5) | C-3 (8) | 0.09 |
| Example 31 | α-4 (100) | Under layer film (1) | B1-2 (1) | B2-1 (0.5) | C-3 (8) | 0.09 |

Evaluation Example 3

Resolution by Exposure to F2 Excimer Laser

Using the composition solutions prepared in the same manner as in Evaluation Example 2, resist films in Examples 32-35 were prepared in the same manner as in Examples 18-27 of Evaluation Example 2. Resist films in Examples 36-37 were prepared in the same manner as in Examples 28-31 of Evaluation Example 2. Using an Levensonmask as a reticle, the resist films were exposed to an F2 excimer laser (wavelength: 157 nm, NA=0.60, and σ=0.70) while changing the irradiation dose, post-baked for 90 seconds on a hot plate maintained at 110° C. (Examples 32-35) or at 100° C. in Examples 36-37, and then developed in a 2.38 wt % aqueous solution of tetramethylammonium hydroxide, thereby forming a line-and-space pattern (1L/1S).

The evaluation results are shown in Table 3.

Components in Table 3 other than the polysiloxanes (α) are as described above.

the lithography process that will become more and more minute in the future. Obviously, numerous modifications and variations of the present invention are possible in light of the above teachings. It is therefore to be understood that, within the scope of the appended claims, the invention may be practiced otherwise than as specifically described herein.

The invention claimed is:

1. A radiation sensitive resin composition comprising (A) an acid-dissociable group-containing polysiloxane and (B) a compound which generates an acid of the following formula (I),

(I)

TABLE 3

| | Polysiloxane | | Acid generator (parts by weight) | | Acid diffusion | |
| --- | --- | --- | --- | --- | --- | --- |
| | (α) (parts by weight) | Substrate | B1 | B2 | controller (mol %) (*) | Resolution |
| Example 32 | α-1 (50) α-2 (50) | Si | B1-1 (1) | B2-1 (0.5) | C-3 (8) | 0.07 |
| Example 33 | α-1 (50) α-2 (50) | Under layer film (1) | B1-2 (1) | B2-1 (0.5) | C-3 (8) | 0.07 |
| Example 34 | α-1 (50) α-2 (50) | Under layer film (β-1) | B1-2 (1) | B2-1 (0.5) | C-3 (8) | 0.07 |
| Example 35 | α-1 (50) α-2 (50) | Under layer film (β-1) | B1-2 (1) | B2-1 (0.5) | C-3 (8) | 0.07 |
| Example 36 | α-3 (100) | Under layer film (β-1) | B1-2 (1) | B2-1 (0.5) | C-3 (8) | 0.07 |
| Example 37 | α-4 (100) | Under layer film (β-1) | B1-2 (1) | B2-1 (0.5) | C-3 (8) | 0.07 |

Evaluation Example 4

Resolution by Exposure to Electron Beams

A composition solution was prepared by homogeneously mixing 50 parts by weight of polysiloxane (α-1), 50 parts by weight of polysiloxane (α-2), 900 parts by weight of 2-heptanone, 1 part by weight of acid generator (B1-2), 0.5 part by weight of acid generator (B2-1), and an acid diffusion controller (C-3) in the amount of 8 mol % of the acid generators in total.

The composition solution was applied onto a silicon wafer substrate or a substrate on which the under layer film (β-1) was previously formed by spin coating and pre-baked for 90 seconds on a hot plate at 140° C. to form resist films with a thickness of 100 nm.

The resist films were exposed to electron beams using a simplified electron beam direct drawing apparatus (50 keV, current density: 4.5 A), post-baked for 90 seconds on a hot plate maintained at a temperature of 110° C., and then developed in a 2.38 wt % aqueous solution of tetramethylammonium hydroxide, thereby forming a line-and-space pattern (1L/1S) to evaluate the resolution.

The both resist films were confirmed that the pattern was resolved to a line size as fine as 0.07 μm.

The radiation-sensitive resin composition of the present invention exhibits superior resolution, while maintaining high transparency to radiations and high dry etching resistance. The resin composition thus can greatly contribute to wherein each Rf individually represents a fluorine atom or a trifluoromethyl group, and wherein Ra is:

a substituted or unsubstituted monovalent cyclic hydrocarbon group having 3-20 carbon atoms;

a substituted or unsubstituted monovalent cyclic fluorohydrocarbon group having 3-20 carbon atoms; or a group of any one of the following formulas (16)-(22):

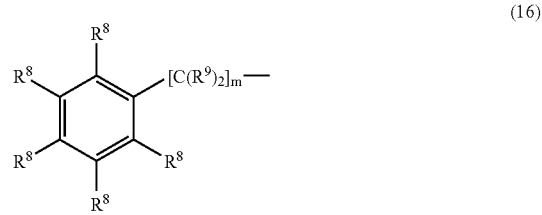

(16)

wherein $R^8$ individually represents a hydrogen atom, halogen atom, hydroxyl group, acetyl group, carboxyl group, nitro group, cyano group, primary amino group, secondary amino group, linear or branched alkoxyl group having 1-10 carbon atoms, linear or branched alkyl group having 1-10 carbon atoms, or linear or branched fluoroalkyl group having 1-10 carbon atoms, $R^9$ individually represents a hydrogen atom, halogen atom, linear or branched alkyl group having 1-10 carbon atoms, or a linear or branched fluoroalkyl group having 1-10 carbon atoms, and m is an integer of 0-10,

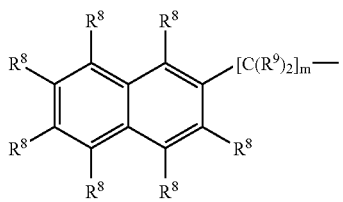 (17)

wherein $R^8$, $R^9$, and m are the same as defined in the formula (16),

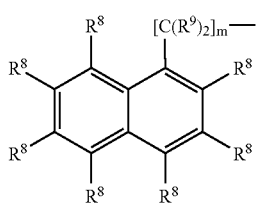 (18)

wherein $R^8$, $R^9$, and m are the same as defined in the formula (16),

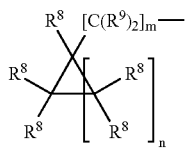 (19)

wherein $R^8$, $R^9$, and m are the same as defined in the formula (16), and n is an integer of 1-18,

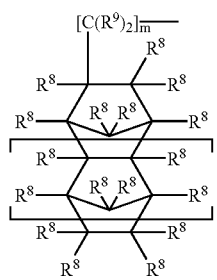 (20)

wherein $R^8$, $R^9$, and m are the same as defined in the formula (16), and p is an integer of 0-3,

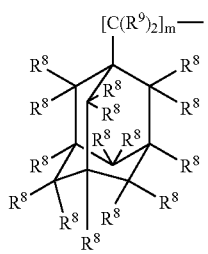 (21)

wherein $R^8$, $R^9$, and m are the same as defined in the formula (16), and

 (22)

wherein $R^9$ and m are the same as defined in the formula (16), and Me is a methyl group.

2. The composition according to claim 1, wherein the acid-dissociable group-containing polysiloxane (A) is a polymer containing at least one of the structural unit of the following formula (1) and the structural unit of the following formula (2),

 (1)

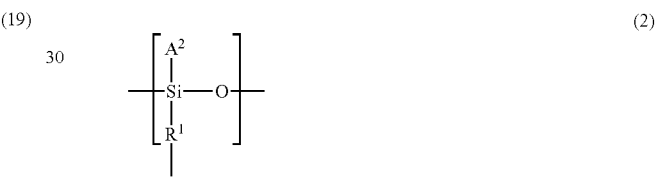 (2)

wherein $A^1$ and $A^2$ individually represent a monovalent organic group having an acid-dissociable group which dissociates by the action of an acid and $R^1$ represents a linear, branched, or cyclic alkyl group having 1-10 carbon atoms or a linear, branched, or cyclic haloalkyl group having 1-10 carbon atoms.

3. The composition according to claim 2, wherein the acid-dissociable group-containing polysiloxane is a polymer having the structural unit of the above formula (1).

4. The composition according to claim 3, wherein the content of the structural unit of the formula (1) in the acid-dissociable group-containing polysiloxane is 5-80 mol % of all structural units.

5. The composition according to claim 3, wherein the content of the structural unit of the formula (1) in the acid-dissociable group-containing polysiloxane is 10-60 mol % of all structural units.

6. The composition according to claim 1, wherein the glass transition temperature of the acid-dissociable group-containing polysiloxane is 0-500° C.

7. The composition according to claim 1, wherein the acid-dissociable group-containing polysiloxane has a polystyrene-reduced weight average molecular weight (Mw) determined by gel permeation chromatography of 1,000 to 10,000.

8. The composition according to claim 1, wherein the acid-dissociable group-containing polysiloxane has a ratio (Mw/Mn) of the polystyrene-reduced weight average molecular weight (Mw) to the polystyrene-reduced number average molecular weight (Mn) determined by gel permeation chromatography (GPC) of the acid-dissociable group-containing polysiloxane of 2.5 or less.

9. The composition according to claim 1, wherein the compound generating an acid of the above formula (I) is an onium salt.

10. The composition according to claim 1, wherein the components are dissolved in a solvent.

11. The composition according to claim 10, the solvent comprises at least one solvent selected from the group consisting of a linear or branched ketone, cyclic ketone, propylene glycol monoalkyl ether acetate, alkyl 2-hydroxypropionate, and alkyl 3-alkoxypropionate.

12. The composition according to claim 10, wherein the solvent is used in an amount to make the total solid content of the solution 1-25 wt %.

13. The composition according to claim 10, wherein the solvent is used in an amount to make the total solid content of the solution 2-15 wt %.

* * * * *

UNITED STATES PATENT AND TRADEMARK OFFICE
CERTIFICATE OF CORRECTION

PATENT NO.        : 7,288,359 B2
APPLICATION NO.   : 10/309017
DATED             : October 30, 2007
INVENTOR(S)       : Haruo Iwasawa, Akihiro Hayashi and Tsutomu Shimokawa It is certified that error appears in the above-identified patent and that said Letters Patent is hereby corrected as shown below:

Column 41:
　　Formula 20 of Claim 1, which appears at column 41, lines 40-50, should include the variable "p" on the right hand side of the lower bracket as follows:

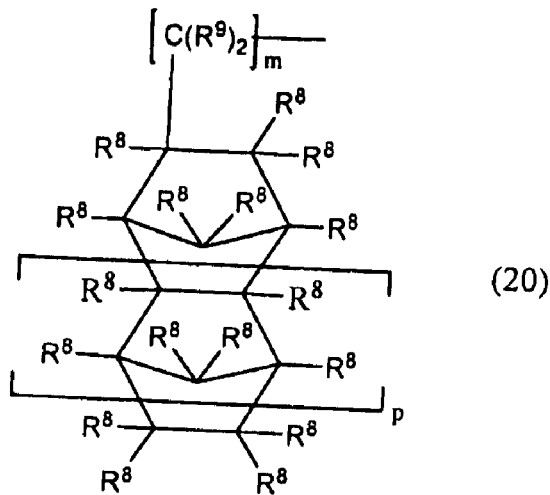

(20)

Signed and Sealed this

First Day of April, 2008

JON W. DUDAS
*Director of the United States Patent and Trademark Office*